US011203570B2

(12) United States Patent
Siepmann et al.

(10) Patent No.: US 11,203,570 B2
(45) Date of Patent: Dec. 21, 2021

(54) VIRTUAL SENSING METHOD AND SYSTEM FOR CONTROLLING A COMPOSITION VARIABLE IN A UREA PRODUCTION PROCESS

(71) Applicant: YARA INTERNATIONAL ASA, Oslo (NO)

(72) Inventors: Volker Siepmann, Holsbeek (BE); Lino Giovanni Porro, Etterbeek (BE); Elisa Burgato, Occhiobello (IT)

(73) Assignee: YARA INTERNATIONAL ASA, Oslo (NO)

( * ) Notice: Subject to any disclaimer, the term of this patent is extended or adjusted under 35 U.S.C. 154(b) by 0 days.

(21) Appl. No.: 16/967,152

(22) PCT Filed: Feb. 4, 2019

(86) PCT No.: PCT/EP2019/052648
§ 371 (c)(1),
(2) Date: Aug. 4, 2020

(87) PCT Pub. No.: WO2019/149937
PCT Pub. Date: Aug. 8, 2019

(65) Prior Publication Data
US 2020/0354312 A1    Nov. 12, 2020

(30) Foreign Application Priority Data

Feb. 5, 2018   (EP) .................................... 18155091

(51) Int. Cl.
*C07C 273/04* (2006.01)
*B01J 19/00* (2006.01)
*G05B 13/04* (2006.01)

(52) U.S. Cl.
CPC ......... *C07C 273/04* (2013.01); *B01J 19/0006* (2013.01); *G05B 13/041* (2013.01);
(Continued)

(58) Field of Classification Search
None
See application file for complete search history.

(56) References Cited

U.S. PATENT DOCUMENTS

| 5,573,734 A | 11/1996 | Pagnani |
| 2006/0270872 A1 | 11/2006 | Kojima |

(Continued)

FOREIGN PATENT DOCUMENTS

| EP | 0114442 A1 | 8/1984 |
| EP | 2955506 A1 | 12/2015 |
| WO | 2010137454 A1 | 12/2010 |

OTHER PUBLICATIONS

Ke-Lin Du et al., Simulated Annealing, Search and Optimization by Metaheuristics, 2016, Springer International Publishing Switzerland, pp. 29-36.

(Continued)

*Primary Examiner* — Sudhakar Katakam
*Assistant Examiner* — Jennifer C Sawyer
(74) *Attorney, Agent, or Firm* — Dilworth IP, LLC

(57) ABSTRACT

The invention relates to a virtual sensing method and system for controlling at least one composition variable in a urea production process, based on a plurality of online measured process variables and a model, wherein the model is used to estimate, during the urea production process, the at least one composition variable indicative of a urea content on the basis of the plurality of online measured process variables, and modifying at least one of the plurality of online measured process variables for ensuring that a value of the at least one composition variable is within a predetermined range. The invention also relates to determining the model.

7 Claims, 13 Drawing Sheets

(52) U.S. Cl.
CPC .............................. *B01J 2219/002* (2013.01); *B01J 2219/00186* (2013.01); *B01J 2219/00243* (2013.01)

(56) References Cited

U.S. PATENT DOCUMENTS

2009/0149981 A1   6/2009   Evans et al.
2014/0365195 A1   12/2014   Lahiri et al.

OTHER PUBLICATIONS

International Preliminary Report on Patentablility issued in International Patent Application No. PCT/EP2019/052648 dated Jun. 8, 2020.
International Search Report and The Written Opinion issued in International Patent Application No. PCT/EP2019/052648 dated Apr. 16, 2019.

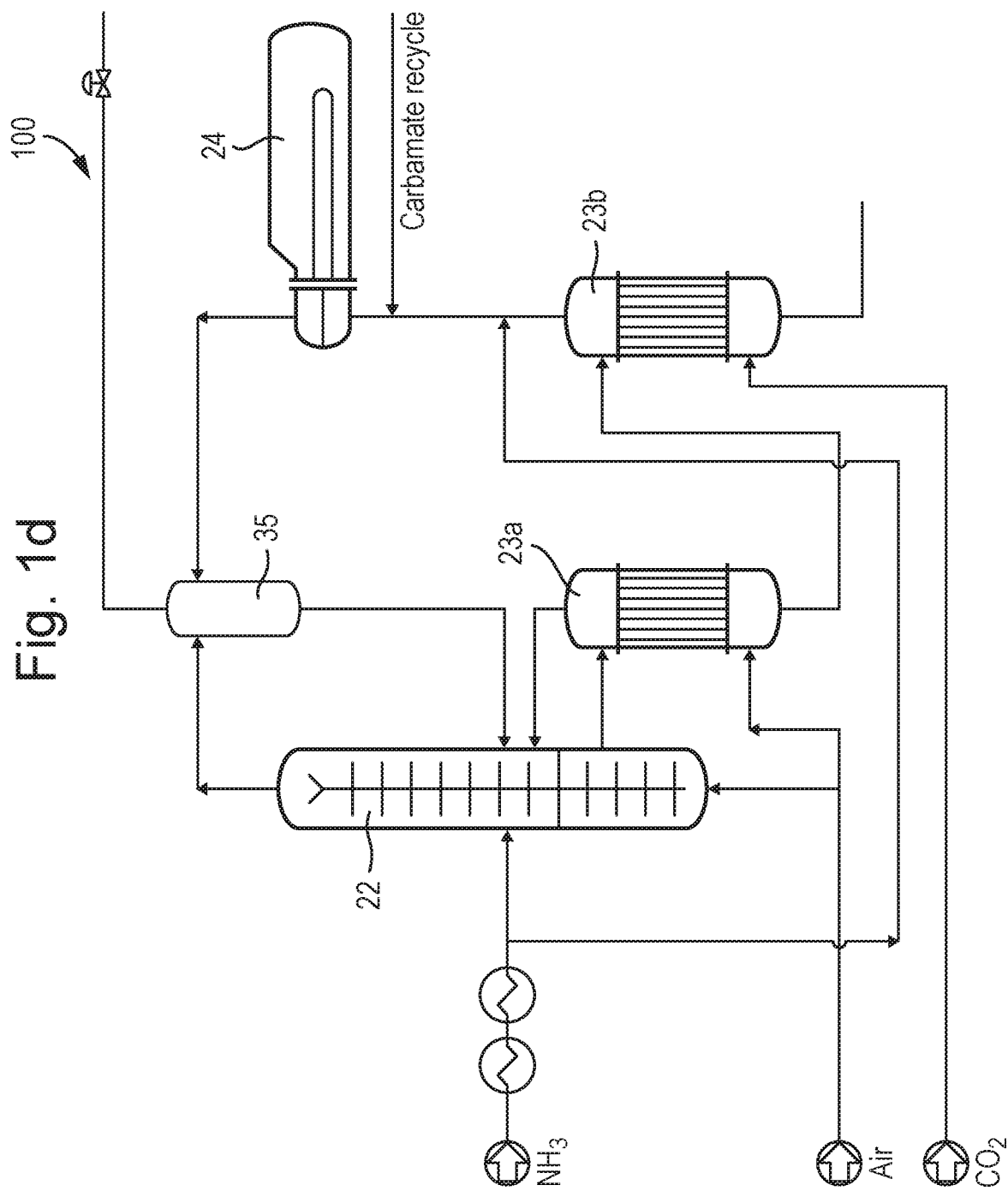

Fig. 3

VIRTUAL SENSING METHOD AND SYSTEM FOR CONTROLLING A COMPOSITION VARIABLE IN A UREA PRODUCTION PROCESS

FIELD OF THE INVENTION

The invention relates to a virtual sensing method and system for controlling at least one composition variable in a urea production process. The invention further relates to a virtual sensing method and system for obtaining a model for controlling at least one composition variable in a urea production process. Furthermore, the invention relates to a computer system.

BACKGROUND TO THE INVENTION

Urea is an important chemical product which is mainly utilized as fertilizer. It can be produced by the reaction between ammonia and carbon dioxide at high pressure (e.g. 13-30 MPa) and high temperature (e.g. 180-200° C.). Different types of processes for the production of urea exist. In a total recycle process, all the ammonia leaving a synthesis section is recycled to the reactor and an overall conversion of ammonia to urea reaches approximately 99%. Stamicarbon, Snamprogetti and Toyo processes are the well known examples of such process, while Casale is mainly acting to modify some of these technologies, by applying proprietaries processes to revamp urea plants capacities. For instance, a urea synthesis plant based on the Stamicarbon process includes a urea reactor, carbamate condenser, stripper and a scrubber. In the carbamate condenser, ammonia ($NH_3$) in liquid phase, carbon dioxide ($CO_2$) in gas phase and liquid ammonium carbamate from the downstream section, partially react to form further ammonium carbamate which is in the liquid phase. This reaction is an equilibrium reaction. The not reacted ammonia and carbon dioxide, together with the liquid ammonium carbamate go to the urea reactor, where ammonia and carbon dioxide continues to react forming ammonium carbamate, which slowly reacts to urea and water. The reaction is slow and it is requiring volume to get residence time.

The solution outlet from the urea reactor passes through a stripper, where not reacted carbamate is decomposed to ammonia and carbon dioxide thanks to the heat given by steam on the shell side and ammonia stripped off by the carbon dioxide fed to the stripper bottom. Stripped gases are fed to the carbamate condenser. In order to achieve an optimum yield of urea from the urea reactor, it is desired that in the stripping urea process, the reactants are present at an optimum specific ratio since this can lead to a stable operation of the urea synthesis section, minimum consumption of energy and/or maximum yield of urea. One of the key parameters to control this is a molar ratio N/C in the urea reactor, which is defined as a ratio between the total equivalent $NH_3$ and the total equivalent $CO_2$ in the reactor. The stability of this parameter is affecting stability of the downstream section and consumptions.

Typically, only a limited number of possibilities to analyze a composition variable of the urea production plant are available. For instance, when the composition variable is chosen to include the N/C ratio, certain challenges may be encountered. Often, the urea synthesis plant operates by taking manual samples to do a laboratory analysis, but safety risks and inaccuracies are inherently connected to the high pressure of the process. Samples are for instance taken multiple times a day, e.g. twice a day. Then the operator(s) needs to wait for an extended period of time, for instance for 4 to 6 hours, before obtaining lab results for the N/C ratio, after which it is possible to act upon process variables, such as a feed of $NH_3$ and/or $CO_2$ into the urea production plant so as to correct the N/C ratio. Alternatively, a dedicated measurement instrument can be installed which is able to measure the N/C ratio, for instance by means of a correlation with the density. The density of a urea reactor effluent stream is known to be linear with the N/C ratio under certain temperature and pressure conditions (see e.g. US 2006/0270872 A1, Yasuhiko Kojima, 30 Nov. 2006). However, such dedicated measurement instruments are typically expensive and require maintenance.

The process complexity can yield strong integrations, and possibly also longer response times and difficulty to understand process dynamics. Controlling the process towards a stable operation is a major challenge. Therefore, there is a need for improving the operation of a urea production process.

The inventors have now established a virtual sensing method, in particular an empirical virtual sensing method, which excludes the use of any composition parameter as input variable, either online or offline measured, and is based exclusively on a plurality of online measured process variables and a model.

Virtual sensing techniques, also called soft sensing, proxy sensing, inferential sensing, or surrogate sensing, are generally used to provide feasible and economical alternatives to costly or impractical physical measurement instrument. A virtual sensing system uses information available from other measurements and process parameters to calculate an estimate of the quantity of interest. While a variety of virtual sensing techniques are available, the vast majority of these can be classified as either analytical techniques where the calculation of the measurement estimate is based on approximations of the physical laws that govern the relationship of the quantity of interest with other available measurements and parameters, or empirical techniques where the calculation of the measurement estimate is based on available historical measurement data of the same quantity, and on its correlation with other available measurements and parameters.

US 2006/0270872 A1 (Yasuhiko Kojima, 30 Nov. 2006) discloses a method for synthesizing urea which includes a step of measuring the density of a condensed liquid (i.e. a composition variable) and calculating the N/C value of the condensed liquid based on a measured temperature, the determined density and a mathematical relationship between them.

US 2009/0149981 A1 (Evans et al., 11 Jun. 2009) discloses a system for continuous near real time online monitoring of a chemical plant or refinery. The method of monitoring is based on a multi-variate statistical model developed using off-line, selected process-specific historical process data. The method is a passive method focussed on monitoring, rather than controlling, a variable in a process, and it can be based on both process and composition variables, measured off-line and online, and has not been used for controlling at least one composition variable in a urea production process exclusively based on a plurality of online measured process variables and a model, including the step of modifying at least one of the plurality of online measured process variables for ensuring that a value of the at least one composition variable is within a predetermined range.

SUMMARY OF THE INVENTION

It is an object of the invention to provide for a virtual sensing method and a system that obviates at least one of the above mentioned drawbacks.

Alternatively, or additionally, it is an object to provide an improved, or at least alternative, virtual sensing method of controlling a urea production process. Thereto, according to an aspect is provided a virtual sensing method for controlling at least one composition variable in a urea production process, exclusively based on a plurality of online measured process variables and a model, wherein the model is used to estimate, during the urea production process, at least one composition variable on the basis of the plurality of online measured process variables, wherein the method includes modifying at least one of the plurality of online measured process variables for ensuring that a value of the at least one composition variable is within a predetermined range, wherein the model is obtainable by retrieving, over a first period of time during the urea production process, a plurality of online measurement data relating to a plurality of predetermined process variables by means of a plurality of sensors arranged in the urea synthesis plant, the plurality of predetermined process variables comprising at least one of the group consisting of a flow rate, a liquid level, a temperature, and a pressure; retrieving, at time points within the first period of time, a plurality of offline measurement data of the at least one composition variable; and processing the plurality of online and offline measurement data and performing a statistical analysis for identifying the model for predicting the at least one composition variable on the basis of the plurality of predetermined process variables.

Within the context of the invention, with "exclusively based on a plurality of online measured process variables and a model" is meant that the parameters of the model are exclusively online measured process variables, and do not contain off-line measured process variables, nor any composition variable, such as density, pH, conductivity and the like, measured either off-line or online.

The at least one composition variable in the urea production process can be controlled on the basis of the data measured online and the previously determined model. It will be appreciated that the model can be obtained or determined separately from the method of controlling the urea production process. For instance, the model can be already pre-determined and used for controlling process parameters of the urea production process. The online measured data can be obtained directly from the process (without laboratory intervention). The online measured data can be obtained in real time.

Typically, production of the urea end product in a urea production process is the most efficient at a specific N/C ratio or within a predetermined range of N/C ratios. Advantageously, the process parameters are adapted to improve urea end product production. The composition variable to be estimated can be indicative of a urea content. The composition variable to be estimated can be the N/C ratio. It is appreciated that other composition variables than the N/C ratio can also be employed, such as e.g. an H/C ratio, defined as a ratio between a total $H_2O$ and a total $CO_2$, and/or an extent of reaction defined as a ratio between urea and total $CO_2$.

Advantageously, by using the model, measuring the N/C ratio in the urea reactor by sample analysis or dedicated online instruments may no longer be necessary. Hence, it may no longer be required to manually take samples, often involving increased safety risks, for performing offline experiments in a lab. Hence, less time and resources are needed for controlling the urea production process by means of the model. Additionally, or alternatively, it may also no longer be required to provide for online measurement units to measure a composition variable, which can be implemented in the urea production process and which themselves can provide an (accurate) indication of the relevant composition variable, e.g. N/C ratio. In this way, the costs involved can be reduced, since such measurement units are typically expensive, require a great deal of maintenance and/or are often difficult to implement in an existing urea synthesis plant.

The model can be considered as a mathematical model which is configured to use a number of process parameters, in the form of a plurality of online measured process variables, which affect the at least one composition variable in urea production process, such as for instance the N/C ratio. In an advantageous way, using the model the N/C ratio can be predicted without needing to wait for the lab analysis. Hence, the control of the urea production process can be enhanced, so that also the efficiency of the urea synthesis process can be improved. The model may be determined for a high pressure part of a urea synthesis plant.

The method can thus be used for controlling an operation of a urea synthesis plant. Modifying the at least one process variable can include adjusting a current process variable in the urea production process based on the predicted at least one composition variable using the model. The urea concentration from the synthesis section can be considered as an operational outcome of the urea production process. The urea concentration can relate to the at least one composition variable, which is predicted based on the model. During the urea production process, the settings of the chemical urea synthesis plant can be modified for improving the operational outcome. The process variables are selected for setting a regime in which, in accordance with the model, the urea synthesis process outputs a desired composition variable being within the predetermined range.

The urea production process can be controlled towards a stable steady-state operation by means of the model. Optionally, a statistical method is employed for obtaining a linear steady-state model for predicting the at least one composition variable. The N/C ratio can be chosen as the composition variable in the urea production process.

Optionally, the plurality of online measured process variables obtained by means of online measurements over a second period of time, different from the first period of time, are provided as inputs to the identified model, wherein the model provides as an output at least one predicted composition variable, which is being controlled.

The model can be obtained or determined in advance, i.e. using online and offline measurement data obtained during the first time period. The first time period can also be considered as a model building period, in which sufficient data is gathered over a period of time (e.g. weeks, months) to build the model. When the model has been obtained or determined, it can be used for predicting the composition variable based on the online measured process variables provided as input. In this way, the model can determine which configuration of process variables are to be used to obtain an optimum (model predicted) composition variable. Optionally, by means of performing (less frequent) offline measurements, the model can be updated continuously. More measurement points may improve the accuracy of the model, compensate for changes in the urea synthesis plant and/or changes in ambient conditions.

Optionally, the predetermined process variables at least include one or more reactor temperatures, an interplay between hydrostatic pressure of reactor fluid, and a synthesis fluid circulation flow. These process variables are found to be important for determining an accurate model for predicting the at least one composition variable (e.g. N/C ratio), based on the online measured process variables of the urea synthesis process.

Optionally, transient behavior is not captured by the identified model.

Optionally, gathered sensor data from online measurements are stored in a data store, wherein a reduced data set is obtained from the data store, wherein the model is identified based on the reduced data set, the model providing a correlation between the reduced data set and the at least one composition variable.

The plurality of online measured process variables can be sampled down in different ways, for instance by averaging over time (e.g. over 5 minute time intervals). Optionally, a computer program product is used which is configured to collect, optionally arrange, and down-sample large quantities of available raw plant data relating to the plurality of online measured process variables which are measured in high resolution by means of the plurality of sensors.

Optionally, the composition variable is at least one of the group comprising, or e.g. consisting of, a N/C ratio defined as a ratio between a total $NH_3$ and a total $CO_2$, a H/C ratio defined as a ratio between a total $H_2O$ and a total $CO_2$, and/or an extent of reaction defined as a ratio between urea and total $CO_2$.

Optionally, the process variable is at least one of the group comprising, or e.g. consisting of, a $CO_2$ feed flow, $CO_2$ flow to $CO_2$ stripper, a passivation air flow to reactor, a passivation air flow to any stripper, a carbamate recycle flow to carbamate condenser, a carbamate recycle flow to HP scrubber, a steam flow from carbamate condenser, a total flow of $NH_3$, a flow of $NH_3$ to carbamate condenser, a flow of $NH_3$ to carbamate ejector, a flow of $NH_3$ to reactor, a steam consumption of thermal stripper, a steam consumption to $CO_2$ stripper, steam to (any) strippers pressure, synthesis pressure at reactor top, carbamate condenser steam pressure, pressure of $NH_3$ feed, $CO_2$ stripper vapor exit temperature, $CO_2$ stripper liquid exit temperature, temperature of $NH_3$ feed, temperature carbamate, temperature at reactor top, temperature at middle of reactor, temperature of urea solution from reactor, temperature at bottom of reactor, thermal stripper vapor exit temperature, thermal stripper liquid exit temperature, pressure difference in urea reactor outlet valve, liquid level in reactor, liquid level in HP Scrubber, liquid level in HP Separator.

Optionally, a set of 2 to 6 process variables is used. In this way, over-parametrization and dependency on a large number of online measurement devices can be avoided. Optionally, a set of 2, 3, 4, 5 or 6 process variables is used.

Optionally, a set of process variables is used including at least one or more reactor temperatures and a steam flow to a thermal stripper.

Optionally, a set of process variables is used including at least three of a group comprising, or e.g. consisting of, a steam consumption of a first $NH_3$ stripper, a temperature of the urea solution from a reactor, a temperature of the gas outlet of a second $NH_3$ stripper, a temperature of a $NH_3$ feed, and a temperature in the middle of the reactor, and a temperature at the reactor top. In an example, all of these six process variables are used with the model.

Optionally, the statistical analysis comprises an algorithm for performing a principal component analysis or a partial least squares analysis.

Optionally, the algorithm is an orthogonal partial least squares algorithm. An orthogonal partial least squares regression method (OPLS) can be used for obtaining a linear steady-state model for predicting the at least one composition variable. The model may be regarded as an empirical model of the urea synthesis plant. Other techniques such as a correlation analysis, or a multivariate calibration are also possible for obtaining the steady-state model. It is appreciated that the statistical analysis may also include a machine learning algorithm, such as a neural network (learning) algorithm.

Optionally, the urea production process is a Stamicarbon $CO_2$-stripping urea process, a Snamprogetti self-stripping process, a Saipem process, or a $CO_2$ stripping process and/or thermal stripping process, such as an isobaric double recycle process.

The model may use a number of process variables (cf. urea synthesis process parameters) that are affecting the N/C ratio. The N/C ratio can be predicted without waiting for a lab analysis, so that the plant can be controlled in an improved way using the model and measured values of predetermined process variables which are provided as input to the model. In order to establish the mathematical predictive model for the composition variable (e.g. N/C ratio), the following steps can be followed:

1. Collecting measuring points of process variables (tags/parameters of the urea synthesis plant) that are potentially suitable to contribute with information about a selected composition variable, preferably the N/C ratio. Optionally, the predetermined process variables (tags) are chosen to be reliable and situated sufficiently close to the reactor such that the process dynamics and/or delays have a limited impact on the measurements. For instance, twenty-five process variables can be selected for sensing.

2. Retrieving a time series of an actual urea production plant over a first period of time (e.g. a plurality of months) for all the selected (e.g. twenty-five process variable tags). These results can be down-sampled, for example to one hour average values. Optionally, samples of the process variables showing too much variation within that hour may be disregarded. In this way, data only relating to stable runs of the plant can be used for determining the mathematical predictive model. Additionally or alternatively, abnormal operation such as very low production can be disregarded.

3. Optionally, selecting promising process variables out of the total/original number of process variables. For example, six out of the total of twenty-five process variables can be selected to start with.

4. Applying the orthogonal partial least squares (or similar) method so as to find a reliable set of coefficients (a, b, c, . . . ) for the complete, or currently selected, set of process variables.

Furthermore, optionally, an algorithm such as simulated annealing can be applied so as to find the set of the process variables (e.g. set of six) which gives the best quality model. For this purpose, the current set of process variables can be modified randomly for evaluating the quality (by generating a model as in step 4). The modification can then be accepted or rejected with a probability depending on how much it improved the model quality (higher probability) or worsened the model quality (lower probability). The quality can be evaluated by a coefficient of determination, namely an $R^2$ value, which is to be sufficiently close to a predictive error sum of squares, namely a $Q^2$ value, as a result of using a sufficient number of data samples.

Hence, as a result of the above algorithm, process variables of the urea production plant are selected (limited number compared to total amount) for being used with a model for calculating the composition variable, preferably the N/C ratio.

Advantageously, the model can be a mathematical linear steady-state model having a plurality of coefficients linked to a plurality of process variables.

In an exemplary embodiment, the model is given by the following equation:

N/C ratio=$a$×the steam consumption of $a$ first $NH_3$-stripper+$b$×the temperature of the urea solution from the reactor+$c$×the temperature of the gas outlet of $a$ second $NH_3$-stripper+$d$×the temperature of the $NH_3$-feed+$e$×the temperature in the middle of the reactor+$f$×the temperature at the reactor top.

Herein a, b, c, d, e, and f are numerical coefficients. These coefficients, the equation model and the process parameters, can be plant-specific and may depend on the characteristics of the plant.

The urea synthesis/production plant can thus be controlled by using newly measured values of the selected process variables (put in the equation), for estimating the N/C ratio. Based on that, certain parameters of the production process can be changed, for influencing the process variables, so as to control the N/C ratio. For example, if the N/C ratio is going up, then the feed of $NH_3$ in the urea plant can be lowered and vice versa.

According to a further aspect, the invention provides for a method for obtaining a model for controlling at least one composition variable in a urea production process, the method comprising the steps of: retrieving, over a first period of time during the urea production process, a plurality of online measurement data relating to a plurality of predetermined process variables by means of a plurality of sensors arranged in the urea synthesis plant, the plurality of predetermined process variables comprising at least one of the group consisting of a flow rate, a liquid level, a temperature, and a pressure; retrieving, at different time points within the first period of time, a plurality of offline measurement data of at least one composition variable; and processing the plurality of online and offline measurement data and performing a statistical analysis for identifying the model for predicting the at least one composition variable on the basis of the plurality of predetermined process variables.

The model can be usable for controlling a urea production process. Optionally, the method further includes performing simulated annealing for identifying a selection of process variables used with the model, wherein the simulated annealing comprises determining a plurality of process variable sets with different combinations of process variables, and evaluating, for each of the plurality of the process variable sets, a quality of prediction of the at least one composition variable, wherein the process variable set providing the highest quality of prediction of the at least one composition variable is selected for use with the model. The model can be different for different urea synthesis plants.

Optionally, the identified model is further improved by taking into account additional data over a further time period.

According to a further aspect, the invention relates to a system including a controller configured for controlling at least one composition variable in a urea production process, based on a plurality of online measured process variables and a model, wherein the controller is configured to use the model for estimating, during the urea production process, at least one composition variable indicative of a urea content on the basis of the plurality of online measured process variables for ensuring that a value of the at least one composition variable is within a predetermined range, wherein the model is obtainable by: retrieving, over a first period of time during the urea production process, a plurality of online measurement data relating to a plurality of predetermined process variables by means of a plurality of sensors arranged in the urea synthesis plant, the plurality of predetermined process variables comprising at least one of the group consisting of a flow rate, a temperature, a liquid level, and a pressure; retrieving, at different time points within the first period of time, a plurality of offline measurement data of at least one composition variable; and processing the plurality of online and offline measurement data and performing a statistical analysis for identifying the model for predicting the at least one composition variable on the basis of the plurality of predetermined process variables.

Determining the N/C ratio in a urea synthesis plant may be performed offline by means of lab tests/experiments. This is often a slow analysis, such that the feedback is too slow for allowing real-time controlling the urea production process. By using the model it may also no longer be required to put expensive instruments for online measuring of the N/C ratio.

Often, a urea production process already comprises sensors for measuring data relating to a plurality of different process variables (e.g. $CO_2$ feed flow, air to stripper flow, pressure of $NH_3$ feed, temperatures, etc.). This data can now be used together with one or more offline measured composition variables (e.g. N/C ratio) for determining a predictive model. The predictive model can be determined on the basis of a statistical analysis, for example involving carrying out a principal component analysis.

A plurality of different process variables can be measured over a first period of time, and within this first period of time an offline lab test can be carried out for measuring urea solution composition and calculate the N/C ratio. The online measured data of the process variables can then be correlated to the N/C ratio for determining the model. By means of an analysis, such as a principal component analysis, it can be determined which of the process variables correlate best with predicting the N/C ratio. The model may provide an equation for predicting the composition variable (e.g. N/C ratio).

The online measured process variables (e.g. temperature, flow, pressure, etc.) may be measured very easily. Optionally, the influence of the process variables on the composition variable is determined, so that only a selected set of process variables are chosen which strongly correlate with the N/C ratio. In this way, the complexity of the model can be reduced, while providing accurate predictions of the N/C. Typically, the process variables are inexpensive to measure. The model can be regarded as a calibrated model, so that a value of the N/C can be accurately estimated for the particular urea production process using current values of (selected) process variables as input for the model.

According to a further aspect, the invention relates to a system for obtaining a model for controlling at least one composition variable in a urea production process, the system comprising a controller configured to perform the steps of: retrieving, over a first period of time during the urea production process, a plurality of online measurement data relating to a plurality of predetermined process variables by means of a plurality of sensors arranged in the urea synthesis plant, the plurality of predetermined process variables comprising at least one of the group consisting of a flow rate, a liquid level, a temperature, and a pressure; retrieving, at different time points within the first period of time, a plurality of offline measurement data of at least one composition variable; and processing the plurality of online and offline measurement data and performing a statistical analysis for identifying the model for predicting the at least one composition variable on the basis of the plurality of predetermined process variables.

According to a further aspect, the invention relates to a computer system comprising a processor, a memory coupled to the processor, wherein the memory stores a program that, when executed by the processor, causes the processor to perform the method according to the invention.

According to a further aspect, the invention relates to a non-transitory computer-readable medium storing a program that, when executed by processor, causes the processor to perform the method according to the invention.

It will be appreciated that any of the aspects, features and options described in view of the methods apply equally to the systems and the described computer system. It will also be clear that any one or more of the above aspects, features and options can be combined.

BRIEF DESCRIPTION OF THE DRAWING

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawing:

FIGS. 1a-1d show schematic diagrams of embodiments of a urea synthesis plants;

FIG. 3 shows a schematic diagram of an embodiment of a correlation matrix of a model;

DETAILED DESCRIPTION

Figure 1A:
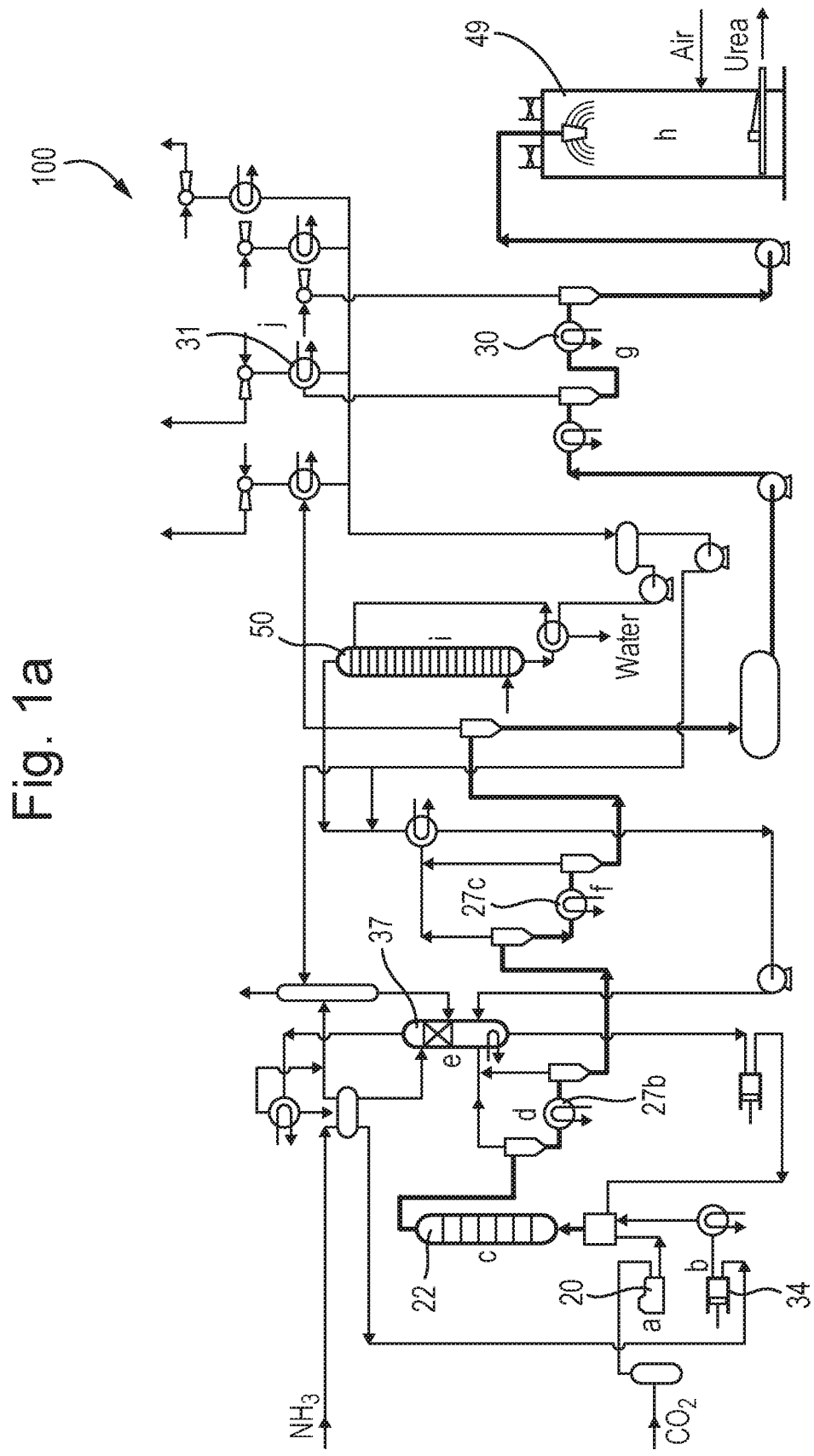

FIG. 1a shows a schematic diagram of an example of a urea synthesis plant 100. In the example of FIG. 1a, it concerns a plant 100 implementing a conventional urea synthesis plant. In this example, the plant 100 includes a $CO_2$ compressor 20, a High-pressure ammonia pump 34, a urea reactor 22, a medium-pressure decomposer 27b, an ammonia-carbamate separation column 37, a Low-pressure decomposer 27c, an evaporation section 30, a finishing Section 49 (in the schematic a prilling section is shown, but as alternative other finishing sections can be installed, such as granulation section, spherodizer section, crystallization section, blending with ammonium nitrate solution to produce liquid urea ammonium nitrate), a waste water treatment 50 (in the schematic a desorber 50 (wastewater stripper) is shown, but as alternative a section including a hydrolizer, to remove traces of urea from water, can be installed) and a vacuum condensation section 31.

Figure 1B:
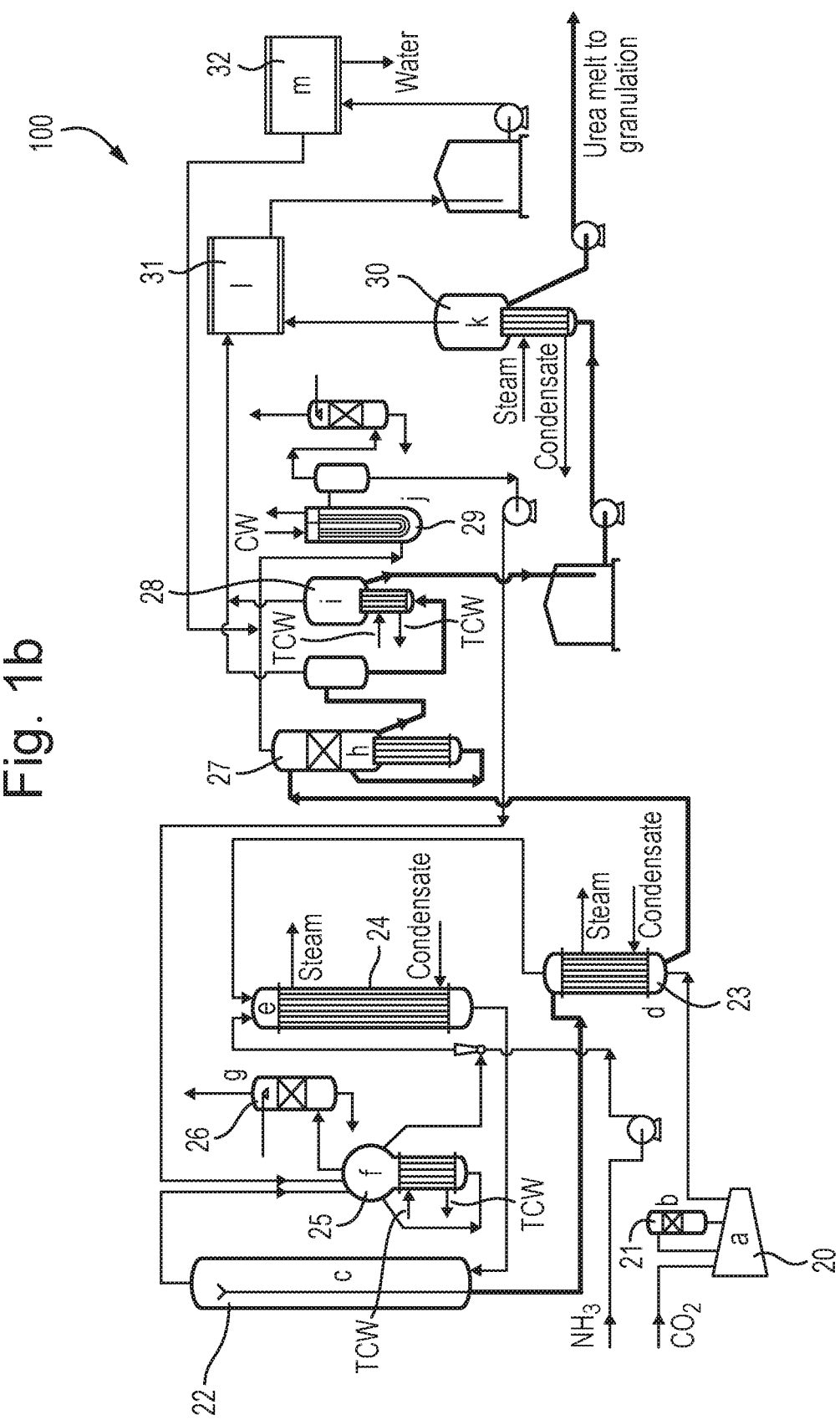

FIG. 1b shows a schematic diagram of an alternative example of a urea synthesis is plant 100. In the example of FIG. 1b it concerns a plant 100 implementing the Stamicarbon $CO_2$-stripping urea process. In this example, the plant 100 includes a $CO_2$ compressor 20, a hydrogen removal reactor 21, a urea reactor 22, a high-pressure stripper 23, a high-pressure carbamate condenser 24 (high pressure carbamate condenser can be alternatively a falling film type as in the schematic or a pool condenser type), a high-pressure scrubber 25, a high pressure carbamate ejector (XX), a low-pressure absorber 26, a low-pressure decomposer and rectifier 27, a pre-evaporator 28, a low-pressure carbamate condenser 29, an evaporation section 30 (alternatively made by one or two evaporators, according if the finishing section is a prilling section, granulation section, spherodizer section, crystallization section, or UAN section), a vacuum condensation section 31, and a process condensate treatment section 32. In FIG. 1b CW indicates cooling water, and TCW indicates tempered cooling water.

Figure 1C:
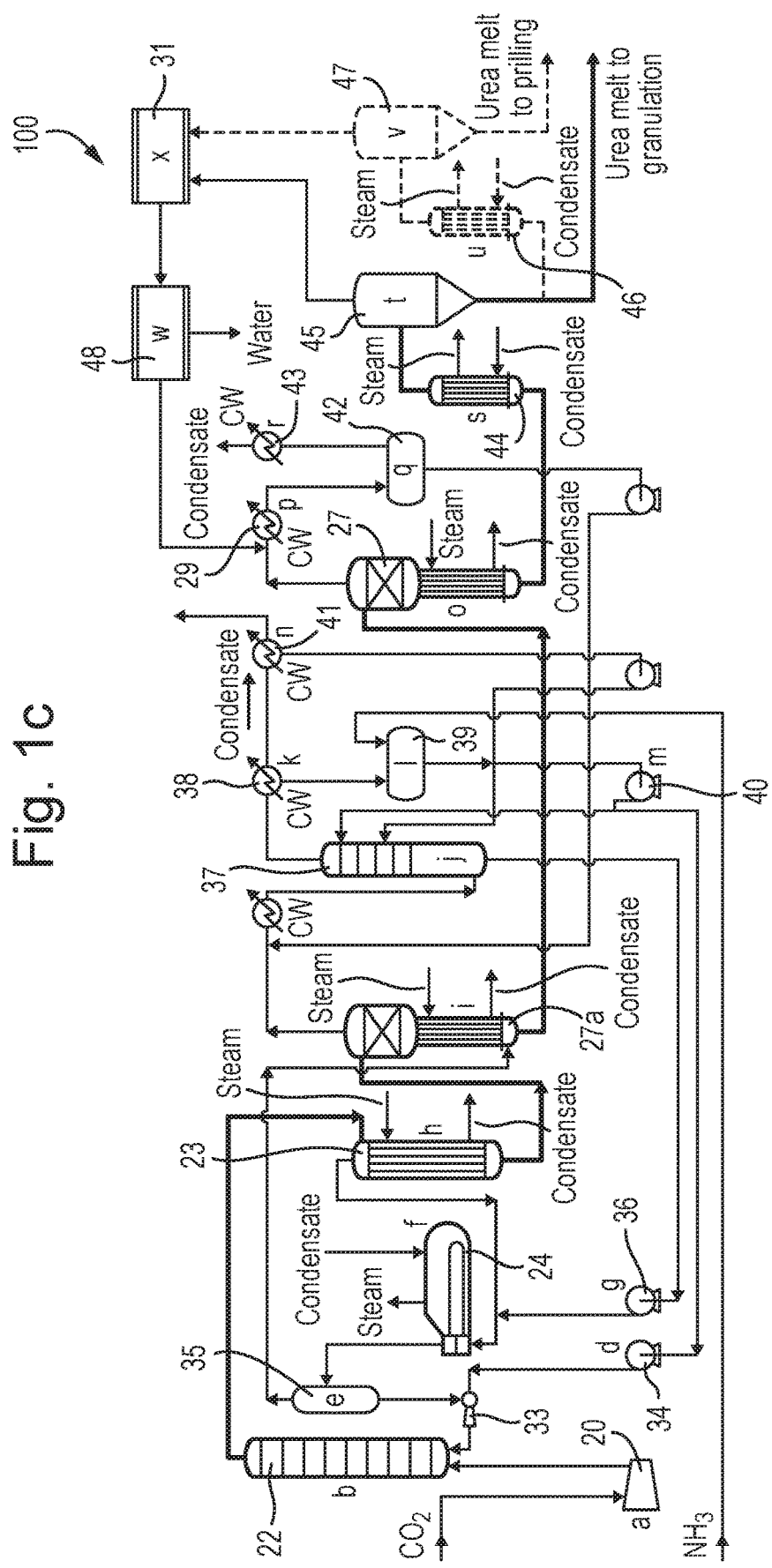

FIG. 1c shows a schematic diagram of an alternative example of a urea synthesis plant 100. In the example of FIG. 1c it concerns a plant 100 implementing the Snamprogetti self-stripping process. In this example, the plant 100 includes a $CO_2$ compressor 20, a urea reactor 22, an high pressure ejector 33, a high-pressure ammonia pump 34, a carbamate separator 35, a high-pressure carbamate condenser 24, a high-pressure carbamate pump 36, a high-pressure stripper 23, a medium-pressure decomposer and rectifier 27a, an ammonia-carbamate separation column 37, an ammonia condenser 38, an ammonia receiver 39, a low-pressure ammonia pump 40, an ammonia scrubber 41, a low-pressure decomposer and rectifier 27, a low-pressure carbamate condenser 29, a low-pressure carbamate receiver 42, a low-pressure off-gas scrubber 43, a first evaporation heater 44, a first evaporation separator 45, a second evaporation heater 46, a second evaporation separator 47, a wastewater treatment section 48, and a vacuum condensation section 31. In FIG. 1c CW indicates cooling water.

The urea synthesis process performed in the plants 100 of FIGS. 1a, 1b 1c and 1d is well known to the person skilled in the art and need not be further elucidated here.

FIG. 1d shows a schematic diagram of an alternative example of a urea synthesis plant 100. The urea synthesis plant 100 may for example be an isobaric double recycle (IDR) process, which can be particularly integrated. In this example, the plant 100 includes a urea rector 22, a thermal stripper 23a, a $CO_2$ stripper 23b, a carbamate condenser 24, a carbamate separator 35

Disturbances in the process generally give composition variations in a part of the synthesis process, and damping these variations via active control can be important for stabilizing the operation of the urea synthesis process at optimal or near-optimal conditions.

The composition of flows in the synthesis process is mainly characterized by the content of $CO_2$, $NH_3$, $H_2O$ and urea in the reactor 22. For convenience, one defines the N/C ratio as the ratio between total equivalent $NH_3$ and total equivalent $CO_2$ and the H/C ratio as the ratio between total equivalent $H_2O$ and total equivalent $CO_2$. The urea content can be stated in terms of weight fraction or extent of reaction, that is the ratio between urea and total $CO_2$. These composition figures are not directly measured. Typically, the costs involved for direct measurement of these composition variables, for example by means of a dedicated measurement unit, are very high. Also integration of such units in existing plants may be challenging.

Online measurements of flows, temperatures, levels and pressures can be analyzed by means of statistical methods to estimate the unknown compositions or composition variables. The predicted composition variables, such as the N/C ratios, can be correlated to the energy consumption of the plant. Combining physical modelling with statistical analysis may provide a model which is not yet sufficiently robust to handle measurement uncertainty.

Moreover, both $CO_2$ and parts of the $NH_3$ may not enter the reactor 22 directly, but e.g. via stripper 23 (23a, 23b), and/or carbamate condenser 24. Additionally, vapors from thermal stripping of reactor effluent may be recycled into the reactor. In such a case, a physical model may be hard to establish, and may not provide sufficient accurate results for establishing a predictive unit operation model of the stripper. On the other hand, often in urea production plants, laboratory analysis samples of the reactor effluent are taken on a regular, e.g. daily, basis. Hence, sufficient plant data may be available. This fact allows to collect a reasonable amount of plant data as a basis for a statistical/empirical model.

In FIGS. 1a, 1b, 1c and 1d an overview of urea production processes in a urea synthesis plant 100 is illustrated. It is appreciated that the method and system according to the invention can also be used with other types of a urea synthesis plant.

For both an empirical model and physical model, the scope of the system plays an important role. A too narrow scope does not capture sufficient process characteristics as a basis for a reliable model for providing accurate estimations or predictions of a composition variable. A too wide scope includes more process noise and dynamics, but also requires a higher number of independent variables, i.e. degrees of freedom, to identify a suitable model.

FIGS. 2a, 2b, 2c and 2d show schematic diagrams of examples of a urea synthesis plant 100. In this figure, potentially relevant instrumentation/sensors for providing online process variable measurements are provided for the exemplary urea synthesis plant 100. It will be appreciated that other types of a urea synthesis plant 100 can also be employed. The sensors can provide online measurements. The table below describes tags linked to the sensors.

| Tag | Process Variable | Unit |
|---|---|---|
| F1 | $CO_2$ feed flow | t/h |
| F2 | $CO_2$ flow to reactor | t/h |
| F3 | $CO_2$ flow to $CO_2$ stripper | t/h |
| F4 | Passivation air to reactor | kg/h |
| F5 | Passivation air to (any) stripper | kg/h |
| F6 | Total carbamate recycle flow | t/h |
| F7 | Steam flow from carbamate condenser | t/h |
| F8 | Total flow of $NH_3$ | t/h |
| F9 | Flow of $NH_3$ to high pressure carb. condenser | t/h |
| F10 | Flow of $NH_3$ to high pressure carb. ejector | t/h |
| F11 | Flow of $NH_3$ to reactor | t/h |
| F12 | Steam consumption of thermal stripper | t/h |
| F13 | Steam consumption of the $CO_2$ stripper | t/h |
| P1 | Pressure of steam to (any) stripper | barg |
| P2 | Synthesis pressure at reactor top | barg |
| P3 | Pressure of steam from carbamate condenser | barg |
| P4 | Pressure of $NH_3$ feed | barg |
| P5 | Pressure of $CO_2$ feed | barg |
| T1 | $CO_2$ stripper vapor exit temperature | ° C. |
| T2 | $CO_2$ stripper liquid exit temperature | ° C. |
| T3 | Temperature of $NH_3$ feed | ° C. |
| T4 | Temperature of $CO_2$ feed | ° C. |
| T5 | Temperature at reactor top | ° C. |
| T6 | Temperature in middle of reactor | ° C. |
| T7 | Temperature of urea solution from reactor | ° C. |
| T8 | Temperature in bottom of reactor | ° C. |
| T9 | Temperature of vapors from reactor | ° C. |
| T10 | Thermal stripper vapor exit temperature | ° C. |
| T11 | Thermal stripper liquid exit temperature | ° C. |
| T12 | Temperature of carbamate to high pressure carbamate ejector | ° C. |
| T13 | Temperature of carbamate to high pressure condenser | ° C. |
| T14 | Temperature of carbamate to high pressure Scrubber | ° C. |
| T15 | Temperature of carbamate to reactor | ° C. |
| DP1 | Pressure difference in valve outlet from reactor | mbar |
| L1 | Liquid level in reactor | % |
| L2 | Liquid level in high pressure scrubber | % |
| L3 | Liquid level in high pressure Separator | % |
| V1 | Valve position for reactor level control | % |

Data analysis may be performed on the obtained laboratory data relating to the offline measured at least one composition variable. The laboratory data may for instance be obtained in a format containing time stamp and molar concentration of $NH_3$, $CO_2$, Urea and/or $H_2O$. For example, the samples may be taken at a time within an interval of approximately 30 minutes of the reported sampling time.

Online measurements, by means of sensors, of the plurality of process variables can be received as event-based raw data having a relatively high time resolution, e.g. down to one sample per second (i.e. 1 Hz). Other sampling frequencies can also be employed. Data can be averaged over, e.g. fixed time, intervals, e.g. before storage. The data can e.g. be averaged over five minute intervals. Online data can be collected for a period of time (e.g. two-hour period) around the nominal analysis sample times (e.g. −90 minutes to +30 minutes). For each offline measurement or laboratory analysis sample, the data may be rejected if
 a. the laboratory analysis does not sum to a value between 97 and 103%;
 b. the online data indicates abnormal operation; and/or
 c. the variation in online data indicates dominating transitional behavior.

As a result, a data-set of validated samples can be obtained, containing both offline measurements (i.e. laboratory measurements) and, e.g. averaged, online measurements (here online-data).

The above steps can be carried out if necessary. Additional steps may be added, or some steps may be omitted. Many of the provided exemplary steps can be considered as optional.

In a next step, the raw laboratory analysis values of the offline measurements can be converted to the desired and algebraic independent mole ratios N/C, H/C and X, here defined as $$N/C = \frac{x_{NH_3} + 2x_{Urea}}{x_{CO_2} + x_{Urea}}$$

$$H/C = \frac{x_{H_2O} - x_{Urea}}{x_{CO_2} + x_{Urea}} \text{ and}$$

$$x = \frac{x_{Urea}}{x_{CO_2} + x_{Urea}}$$

The laboratory analyses are giving weight fractions $w_i$, and these are converted to mole fractions $x_i$ by using molecular weights $M_i$ via $$x_i = \frac{w_i}{M_i}\left(\sum_j \frac{w_j}{M_j}\right)^{-1}$$

Furthermore, a mass feed ratio FR is introduced, relating total $NH_3$ feed to total $CO_2$ feed:

$$FR = \left(\frac{\dot{m}_{NH_3}}{\dot{m}_{CO_2}}\right)_{feed} = \frac{\text{Value of } F8}{\text{Value of } F1}$$

Figure 3:
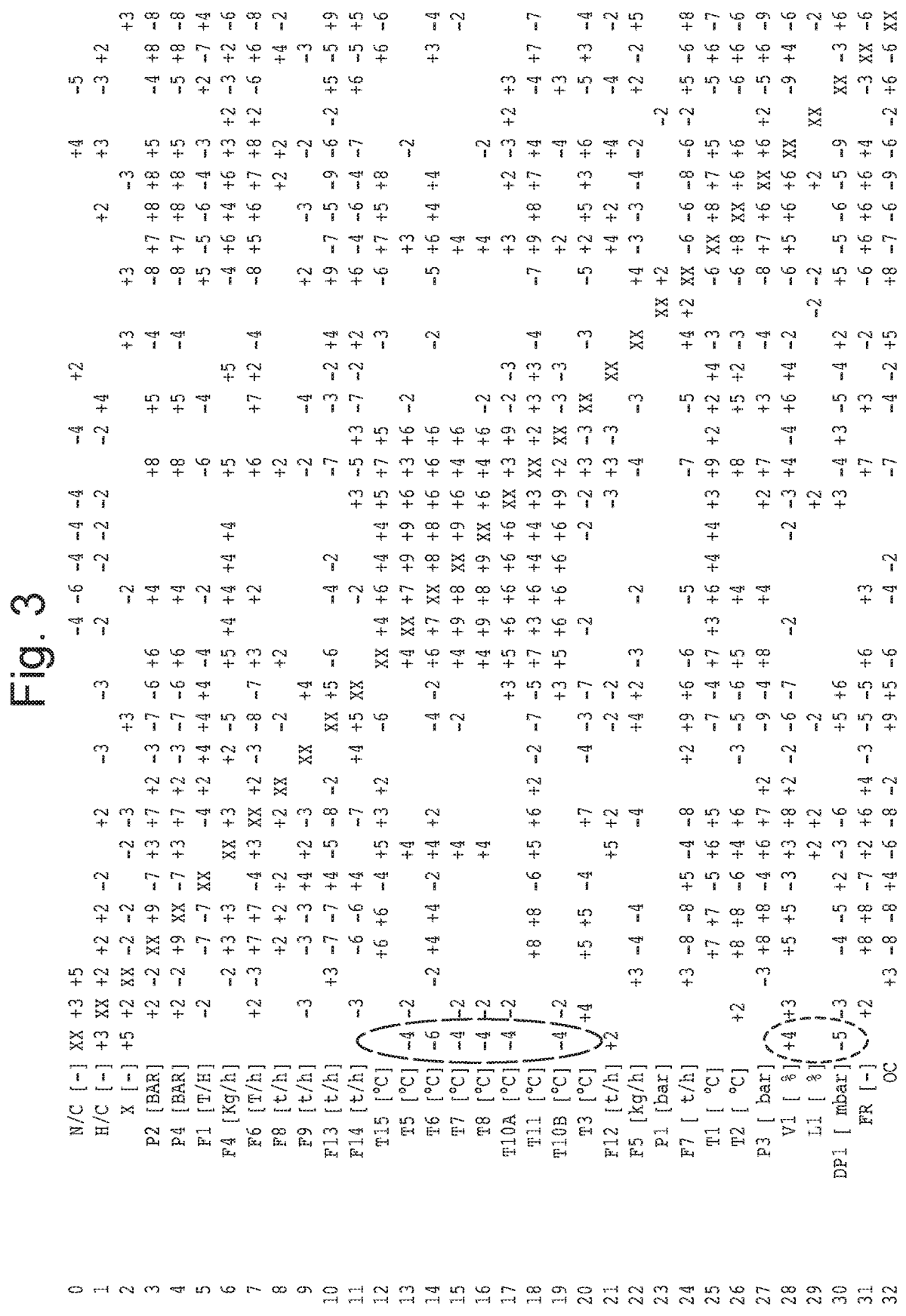

FIG. 3 shows a schematic diagram of an embodiment of a correlation matrix of a model. In this example, a categorical variable OC has been introduced in the data set, defined as zero for all samples before a certain date, and one for all samples beyond that date, to account for a major change in operation conditions were implemented on that certain date. FIG. 3 shows the correlation coefficient matrix for the obtained dataset, wherein the column headers are identical to the row headers. The correlation matrix includes mole ratios from laboratory analysis (see rows 0-2 of the matrix), online measurements (see rows 3-30 of the matrix), and derived variables FR (see row 31 of the matrix) and OC (see row 32 of the matrix). Correlation coefficients (corr) are shown as integers, i.e. floor(10·corr), e.g. +2 means a positive correlation between 0.20 and 0.29. All coefficients with absolute value less than 0.2 are omitted in this example.

In this example, the N/C ratio is well correlated to the reactor temperatures (see rows 12-20, being encircled in the matrix). Moreover, here a pressure drop over a valve between reactor and stripper is found to be an important variable (see rows 28-30, being encircled in the matrix), as it indirectly measures the density of the reactor content. Due to natural circulation with the total head and density as driving force, the liquid level and the pressure drop are coupled via the flow, which is primarily given by other process constraints.

The change of operation conditions (OC) reveals that many process variables were significantly changed, such as synthesis pressure, carbamate recycle flow and steam flow to the $CO_2$ stripper. The analyzed urea content also significantly increased. A most predictive linear model is obtained by fitting a parameter vector p and constant offset $p_0$ to minimize the residuals of the equation:

$$(N/C)_i = p \cdot x_i + p_0$$

for all samples i. Here, $x_i$ is a complete set of available online measurements of the predetermined process variables, as from index 3 to 27 in the exemplary correlation matrix, see FIG. 3. In this example, the resulting model accounts for 78% of the observed variance in N/C. With the given online data, this can be considered as a theoretical limit. The remaining 22% of variance is not correlated to any of the observable process variables, and a major part of it might be measurement noise, uncertainties of laboratory measurements or the like.

To get an understanding of this limit, the variance of laboratory analysis error: $\sigma^2_{lab}$ is considered. The observed $R^2$ value (=0.78) is defined based on variances as $$R^2 = 1 - \frac{\text{var}[(N/C)_{lab} - (N/C)_{calc}]}{\text{var}[(N/C)_{lab}]} = 1 - \frac{\text{var}[(N/C)_{true} - (N/C)_{calc}] + \sigma^2_{lab}}{\text{var}[(N/C)_{lab}]}$$

Even with a perfect model, i.e. $(N/C)_{calc} = (N/C)_{true}$, the limiting condition can be given as $$R^2 < 1 - \frac{\sigma^2_{lab}}{\text{var}[(N/C)_{lab}]} \Leftrightarrow \sigma^2_{lab} < \text{var}[(N/C)_{lab}](1 - R^2)$$

For the given exemplary data set, $\text{var}[(N/C)_{lab}] = 0.0094$, hence $\sigma_{lab} < 0.045$.

A laboratory analysis error in N/C ratio of approximately 0.045 is more than reasonable, as it relates to an error in the individual species analysis of approximate approximately 0.5%.

Hence, for the given exemplary data set, it may not be expected that an identified model reaches a $R^2$ value larger than 0.78, and this value will due to the limited number of samples include false correlations between offline measurement (i.e. laboratory measurement) error and online measurement of process variables.

Furthermore, when utilizing all available online and offline measurements, the regressed model may not be robust against measurement errors and process noise. For instance, the process variable tag P1 receives the coefficient 0.8, hence a realistic pressure variation by approximately 0.5 bar would generate extreme predictions of N/C ratios, that is approximately 0.4.

Advantageously, the total set of independent variables can be reduced to those which are really correlated to the N/C ratio. According to FIG. 3, these are for instance the reactor temperatures and the steam flow to the thermal stripper 22. The reactor temperatures can be strongly correlated to each other. Including all of reactor temperatures as independent variables may trigger the same issues as described above. The following equation represents a reasonable model with three independent variables:

$$\widehat{N/C} = 3.4774 + 0.0120(\bar{T} - 185° \text{ C.}) - 0.071(T_6 - 185° \text{ C.}) + +0.0289(\dot{F}_{12} - 25 t/h) \text{ with}$$
$$\bar{T} = \frac{1}{4}(T_5 + T_6 + T_7 + T_8)$$

This model in this example, however, only explains 44% of the actual variance of N/C ($R^2 = 0.44$). By including the pressure drop and level measurements, the results of this approach can be further improved. However, generally, with the given set of online measurements of the process variables, a compromise can be found between robustness and the predictive properties.

In an advantageous embodiment, a steady-state limitation is implemented for identifying the model. However, alternatively, a dynamic model can be identified based on step response experiments or on reliable physical modelling of process dynamics. The step-test approach may require frequent sampling of synthesis fluid (cf. composition variable) by means of offline measurements, which need to be analyzed in the laboratory. Frequent sampling may not be required when employing a steady-state approach.

With physical modelling, time constants could possibly be estimated to supplement dynamics information to the steady-state gain model obtained by data regression. That is, knowing the steady-state effect of a measured process variable on the N/C ratio by steady-state data analysis, the physical model needs to supply the transient information. Such model could be implemented either by means of for example a state filter (Kalman filter) or as individual delays of measurements using a quasi-steady state model.

A steady-state model can be time-efficient, and more easy to obtain than a dynamic model. This is especially advantageous, since the urea processing plant may comprise numerous recycle flows and therefore very integrated process dynamics. A predictive steady-state model can be provided which does not suffer from the negative effect of transients, which may become amplified, on the predictions of the at least one composition variable, such as for example the N/C ratios.

When the predictive steady-state is implemented into the distributed control system DCS, a steady-state detector could be realized as well, which can be configured to calculate a standard deviation of key measurements over a real-time moving time interval. If this standard deviation is above a certain threshold, defined for each input variable, the predicted N/C ratio values may be flagged or disregarded, since these values may not be accurate (i.e. limited usability of the provided values).

Partial least squares modelling may be employed for obtaining the model. As seen above, a selection of only a few independent variables can result in a significant reduction in $R^2$, while utilizing all measurements can yield a model which is far too sensitive to disturbances. In an advantageous approach not all the selected process variables are treated as independent variables. For instance, it may be beneficial to utilize many of the online tags for the process variables (see above table), but not treat each of the online tags independently. For example, as already indicated in the equation above, the average temperature can be used.

A systematic approach can be provided by means of an (orthogonal) partial least square method (OPLS). The OPLS method transforms the predetermined input variables to maximize correlation with the output variable (N/C). In this way, only the most correlated transformed input variables can be included into the model. An order parameter k can determine how many of these so-called directions are to be included into the model. Therefore, the OPLS method can help obtaining a predictive model without the risk of over-parameterization.

Figure 2A:
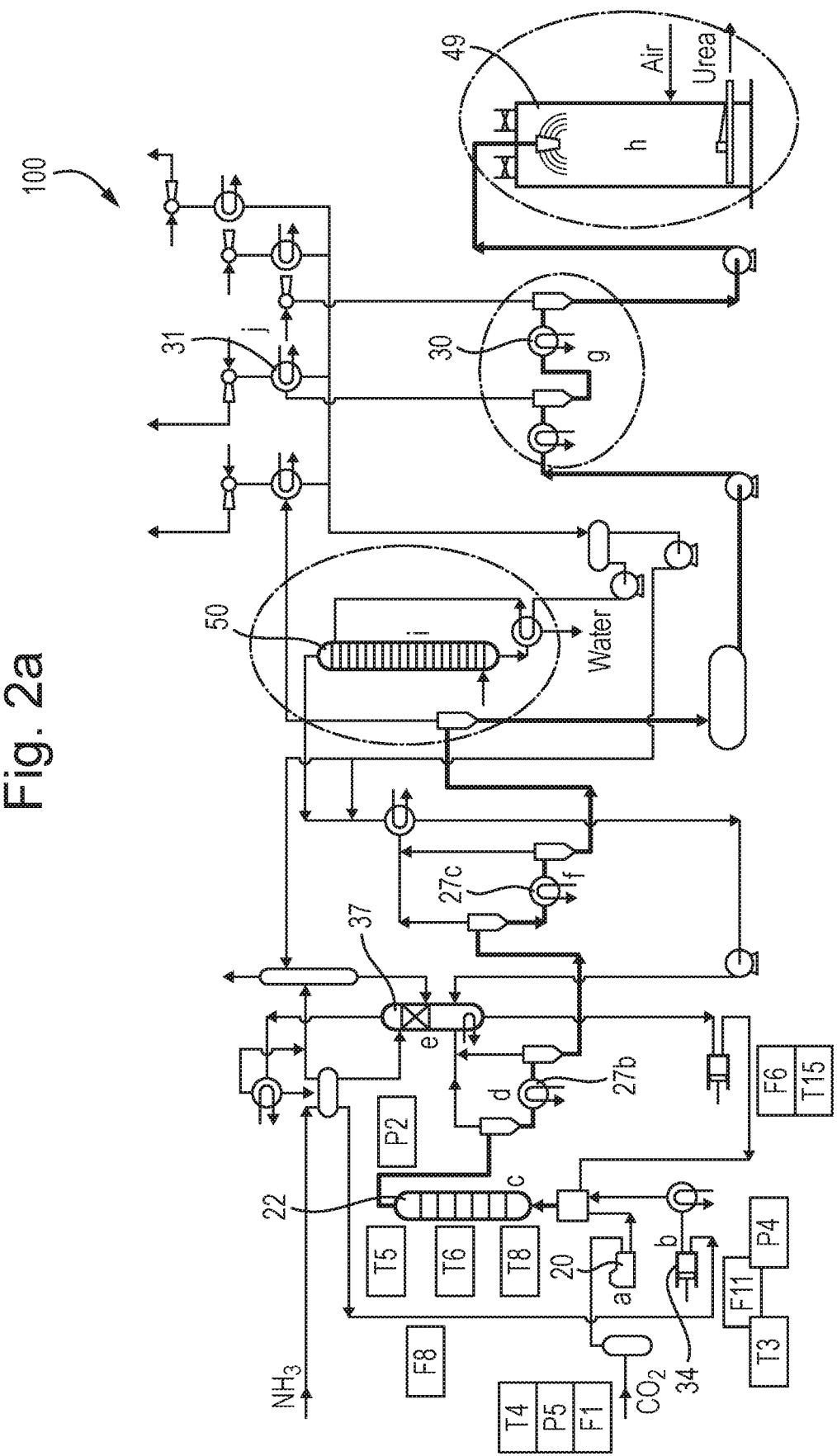
FIGS. 2a-2d show schematic diagrams of embodiments of a urea synthesis plants.
Figure 2B:
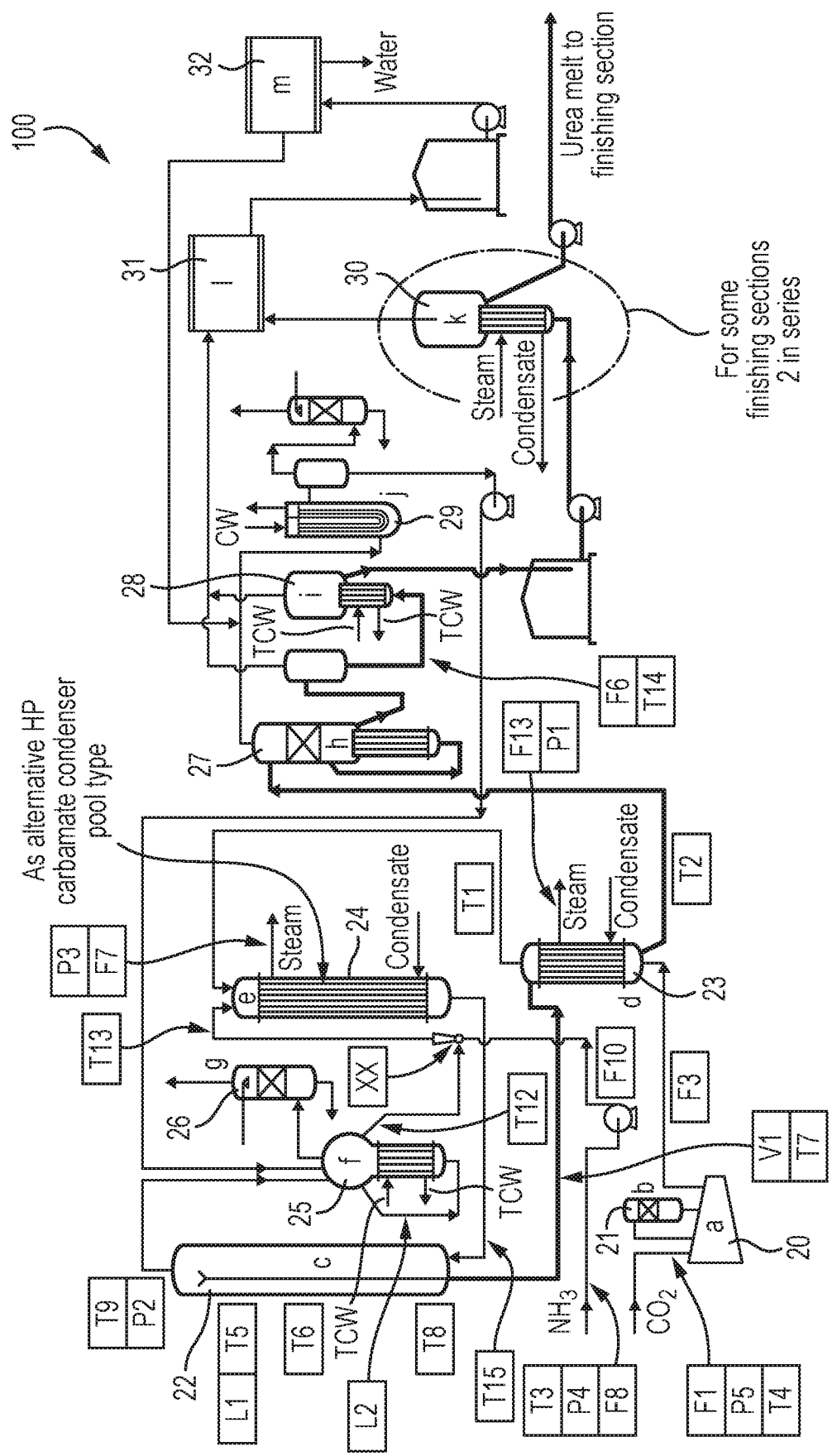
Figure 2C:
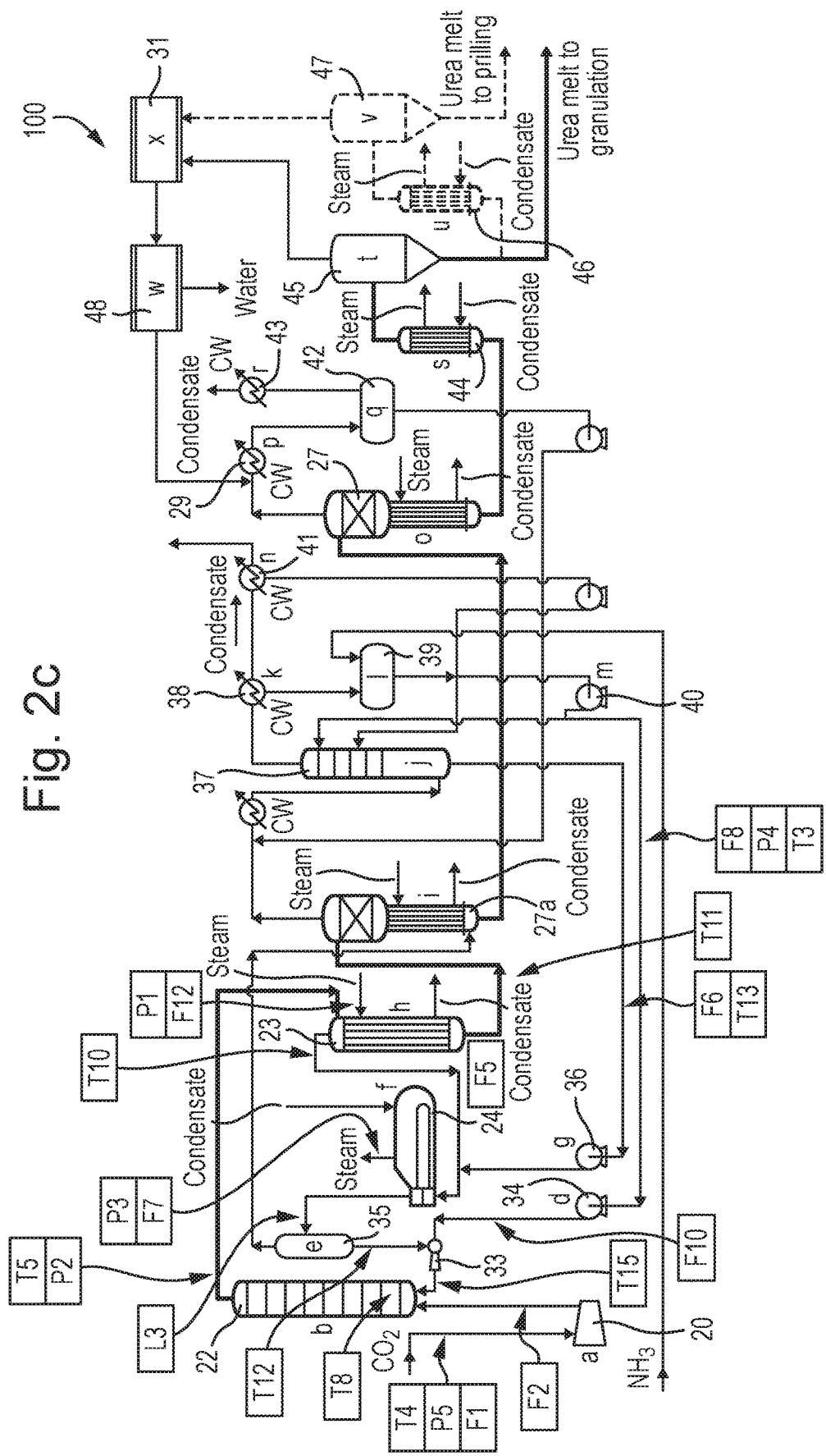
Figure 2D:
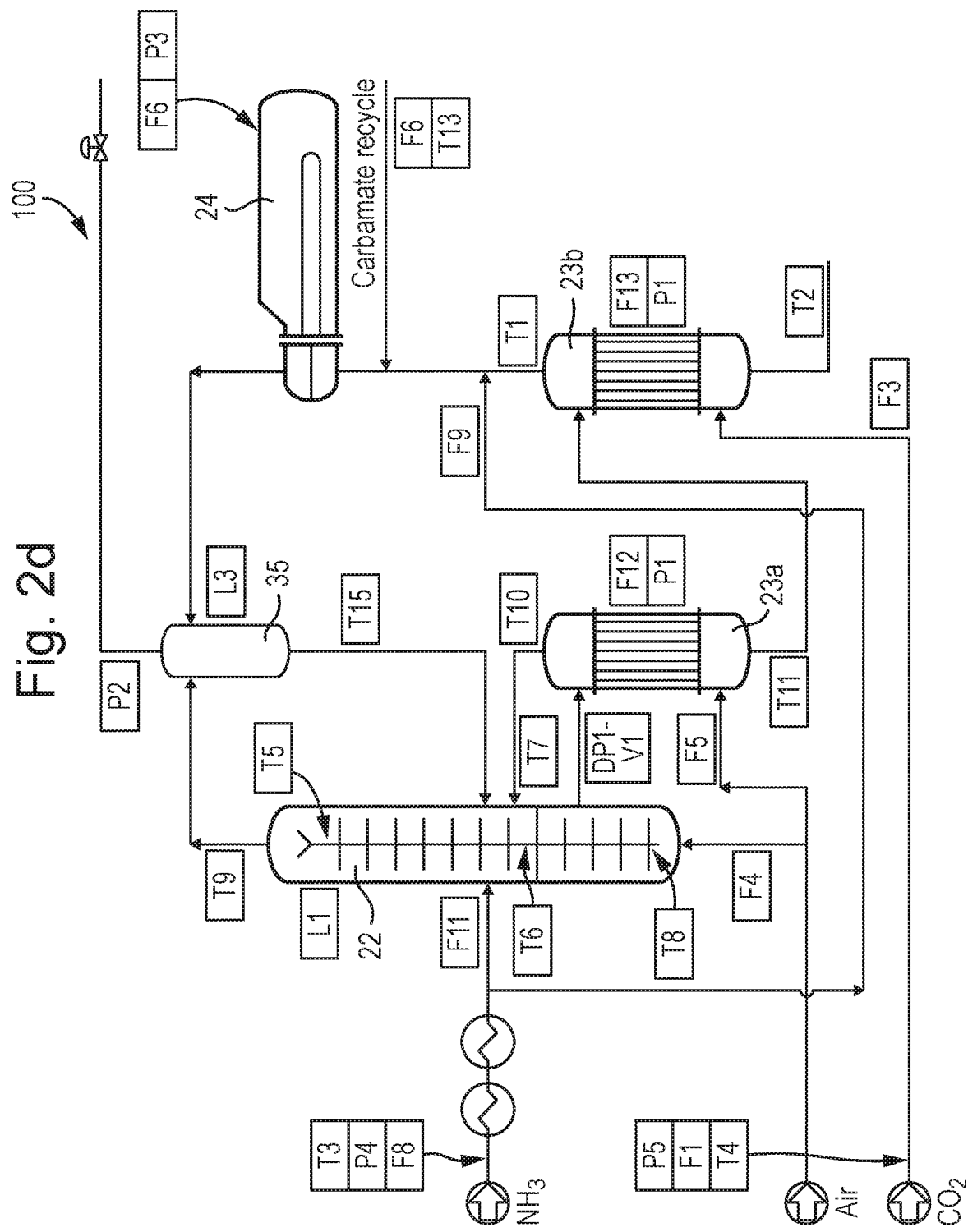

Since for a urea production process, such as for example shown in FIG. 2d, there may be strong correlation among the available online measurements, an input process variable set can be drastically reduced without significant loss of a predictive quality of the model. Additionally or alternatively, in this way, the robustness of the model against failure of measurement signals of the process variables can be improved.

The OPLS method can be used for identifying an initial order of the model, necessary for capturing a significant correlation between the online measured process variables (cf. online measurements) and the offline measured compositions variable(s) (cf. laboratory analyzed N/C ratio). Subsequently, successively one sensor at a time can be removed, selected by its minimal negative impact on model quality.

The OPLS data fit can be repeated in each step. This gives an indication on the model quality in reach for a limited number of sensors involved.

Finally, a (direct sampling) Monte Carlo regression sequence on any combination of sensors can be performed, seeking the maximum $R^2$ value for a model with limited number of sensors used. Other similar techniques may also be employed. Due to strong correlation of online measurements, it can be seen that multiple distinct sets of sensors give very similar results.

The following table gives coefficients of four exemplary models, obtained by running OPLS with k=4 on 8 random sets of measurements as input for the Monte Carlo regression with $10^5$ iterations each.

| Tag x i | Coefficients c_i: (N/C) = C + sum (c_i*x_i) | | | |
|---|---|---|---|---|
| | Model 1 | Model 2 | Model 3 | Model 4 |
| F1 | −0.02450 | −0.02230 | −0.02603 | −0.02641 |
| F13 | 0.01716 | 0.01429 | 0.01625 | 0.01532 |
| P2 | −0.01044 | −0.01117 | −0.01004 | −0.00987 |
| T15 | 0.04584 | 0.04624 | 0.04486 | 0.04625 |
| T6 | −0.06798 | −0.03831 | −0.07175 | −0.07397 |
| T1 | 0.04859 | 0.03295 | 0.04808 | 0.04590 |
| V1 | 0.02942 | | 0.02834 | 0.02799 |
| DP1 | | −0.00533 | | |
| T10B | −0.00432 | | | |
| T7 | | −0.02562 | | |
| P1 | | | 0.00017 | |
| F12 | | | | −0.00285 |
| Constant C | 0.73233 | 4.26689 | 0.94003 | 1.63320 |
| R2 [%] | 70.6 | 70.6 | 70.6 | 70.7 |

All these models are of similar quality, i.e. within $70.6\% \leq R^2 \leq 70.7\%$. The table contains the four best models for an exemplary urea processing plant 100. It can be seen that all models have similar prediction properties.

Figure 4A:
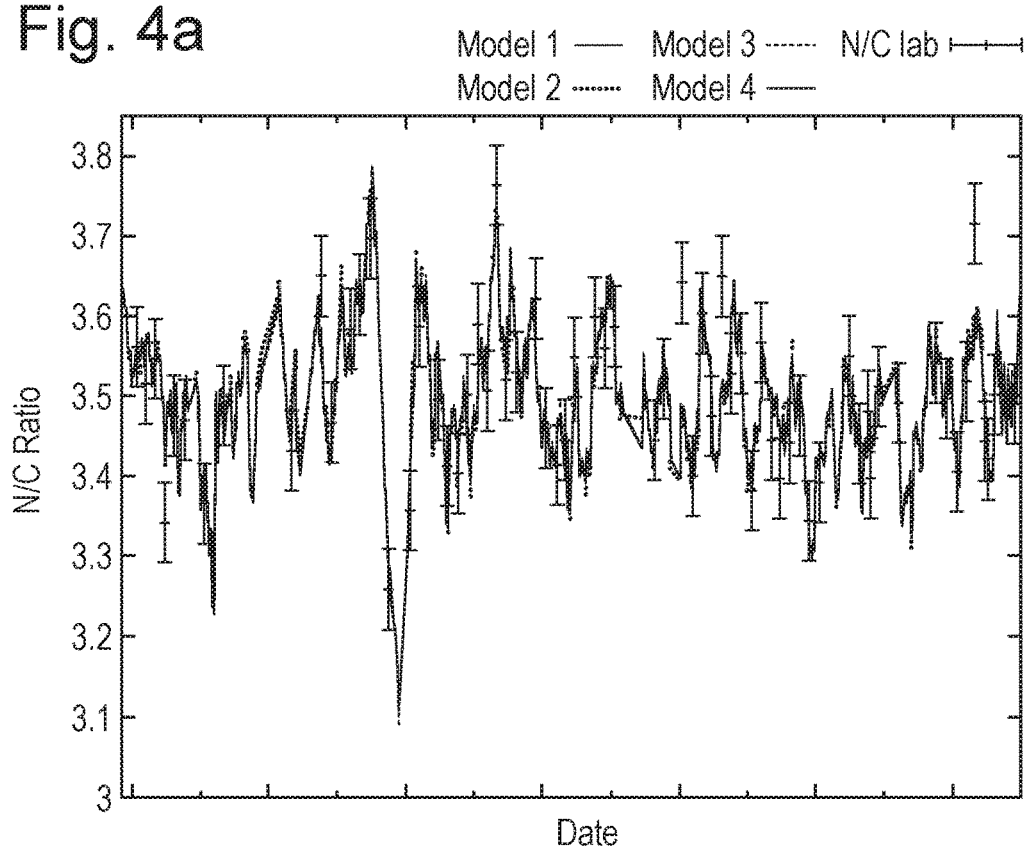
FIG. 4 shows a plot comparing model prediction data with offline measurement data.

FIG. 4(a), (b) shows a plot comparing model prediction data with offline measurement data. It can be seen in FIG. 4(a) that indeed the four different alternative models using online measurement data of a first time period provide similar predictions, closely resembling the offline measurements (N/C lab analyses).

Figure 4B:
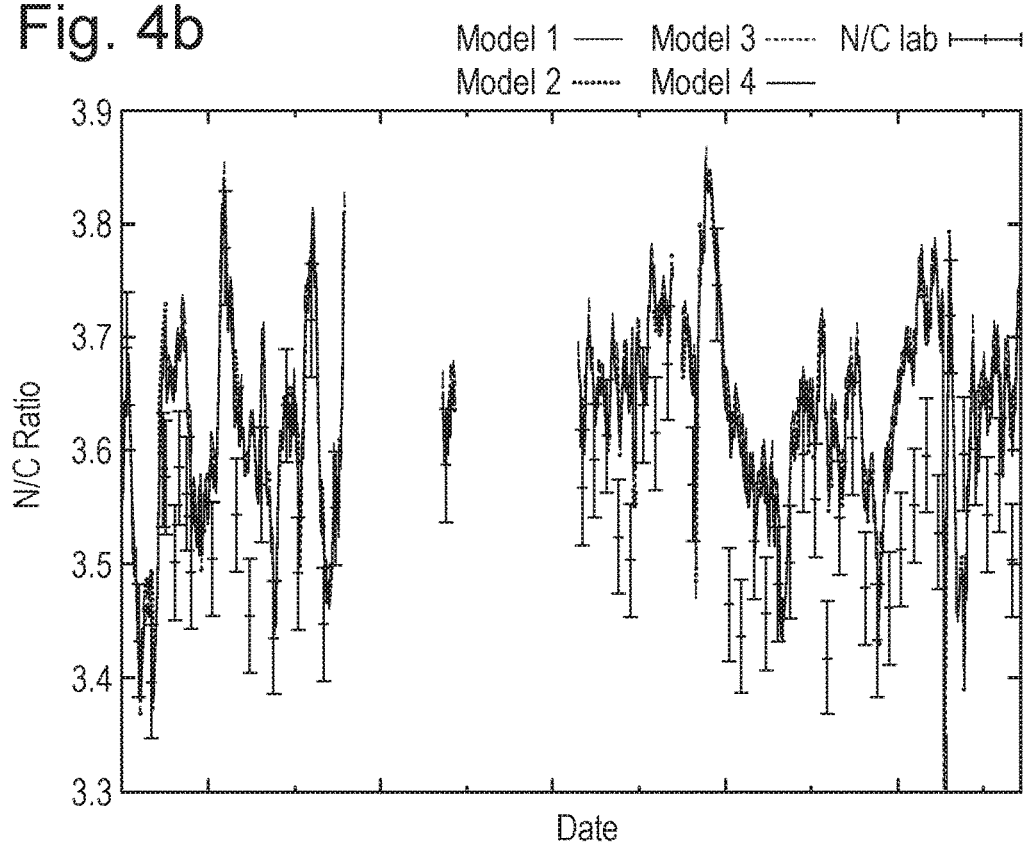

The obtained model can be validated and/or improved, if necessary. In order to validate and/or improve the identified model(s), a second data set can be obtained from the plant, spanning a second time period. The selected set of process variables for building the model can be limited to the most promising candidates of input variables. The periods with available data with regarding offline measurement data (laboratory analysis values) can be combined to obtain a new data set. As can be seen in FIG. 4(b). In this example, due to technical issues, the $CO_2$ feed flow data was not available in some periods, and no predictions could be made within these time intervals, as all identified models rely on this process variable. While the model still predicts the general trends, a clear deterioration is observed, visible as a bias towards higher N/C predictions. Still, the predictions of all four models remain very similar.

An observed deviation (as e.g. shown in FIG. 4(a), (b)) can for example be caused by:
  (a) over-parameterization of the models,
  (b) changes in the urea process
  (c) significant changes in operation, causing non-linear effects, and/or
  (d) utilization of operational handles that have not been used equally much in the calibration period.

Option (a) may be rather unlikely, as only four principle components are used, and many different models (depending on the set of selected input variables) give very similar results. Option (b) cannot be ruled out, but such process changes would normally be less dynamic. Both option (c) and (d) can apply, not least caused by significant changes in ambient conditions especially during the second half of the calibration period. The mitigating action for both latter cases is to improve the models by including the new data samples into the calibration. In this example data, several operational changes were implemented since the start date of the second time period.

FIG. 4(b) shows a plot comparing model prediction data with offline measurement data. This figure provides a model validation with more recent data.

Remodeling can be carried out based on a complete data set. A wider data basis yields a model that is more robust against similar effects in the future, a hypothesis that naturally has to be validated over time. In order to obtain new models, a different approach can be followed than to (only) maximize the $R^2$ value. Due to the lack of calibration data, the priority can be on the predictions of new data, not guaranteed by just maximizing $R^2$. A statistical tool to quantify this property is the calculation of $Q^2$, defined as follows:

1. For all samples (i) in the data set:
    a. Exclude the sample (i) and generate a model using all remaining samples in the data set, in this case using the orthogonal partial least squares method.
    b. Add the deviation of the $i^{th}$ sample $(y_{i,calc}-y_{i,meas})^2$ to a sum denoted as PRESS.
    c. Add the deviation of the $i^{th}$ sample to the mean value $(y_{i,meas}-y_{mean})^2$ to a sum denoted as TSS.
2. Calculate $Q^2=1-PRESS/TSS$, wherein TSS=total sum of squares For over-parameterized models, $Q^2$ rapidly decreases and even becomes negative, that is, the model becomes worse than stating that N/C is constant at its mean value. Maximizing $Q^2$ gives confidence in the predictive properties of the model, but is expensive to calculate, and the Monte Carlo method to find the best set of processing variables (see tags) may no longer yield the optimal solution in reasonable calculation time. Optionally, the optimization method of simulated annealing can be applied to identify the optimal set of tags.

Using six input processing variables (cf. tags), the highest $Q^2$ value for a model can be obtained with e.g. four principal components. The operational changes implemented in the second data set promote use of a different set of input variables. The following table shows the coefficients of an advantageous model for the exemplary embodiment of the urea processing plant 100 of FIG. 2d.

| Tag | Model 5 |
|---|---|
| F12 | −0.009475 |
| T7 | −0.001033 |
| T1 | 0.060801 |
| T3 | 0.008454 |
| T6 | −0.114106 |
| T5 | 0.031956 |
| Constant | 6.022045 |
| $Q^2$ | 0.713018 |
| $R^2$ | 0.0734279 |

Exemplary model 5 is configured to predict N/C ratio, based on the complete set of data.

Clearly, the detected model 5 has a $Q^2$ value very close to $R^2$, meaning that the model will perform predictions just as good as description of calibration data, if the process and/or its operation does not substantially change. This is expected as the model is an empirical model.

Figure 5A:
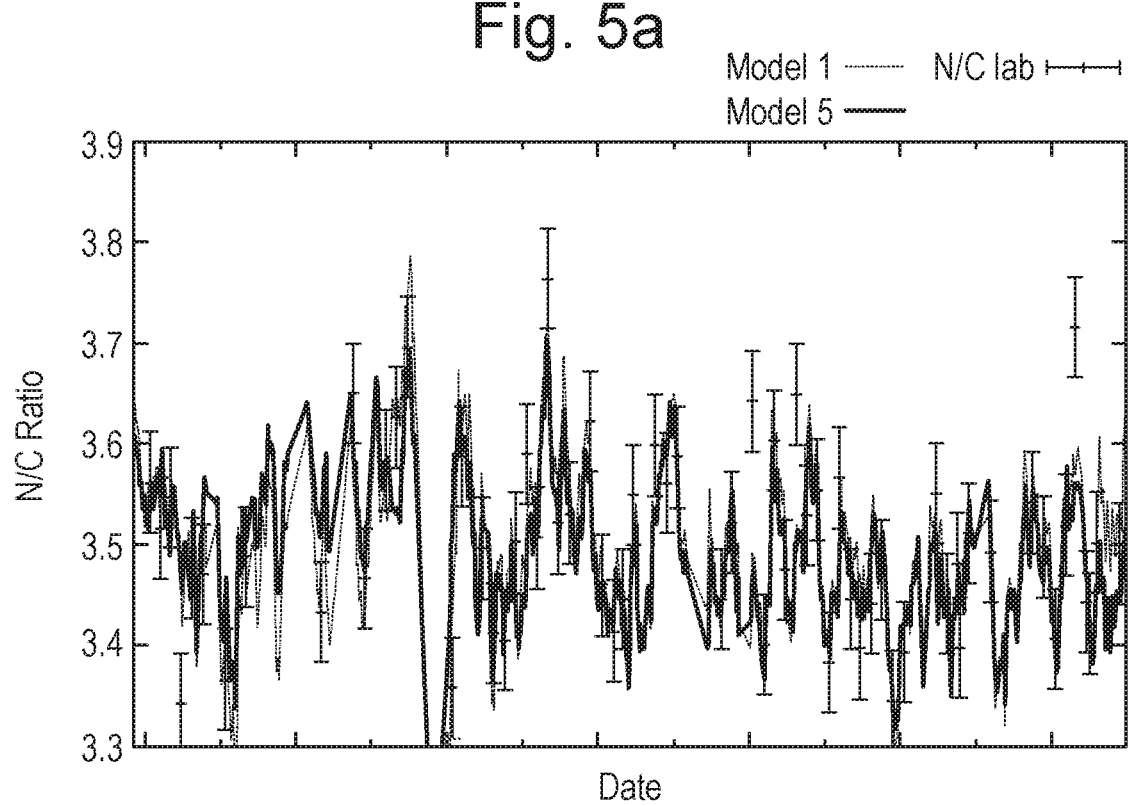
FIG. 5 shows a plot comparing model prediction data with offline measurement data.
Figure 5B:
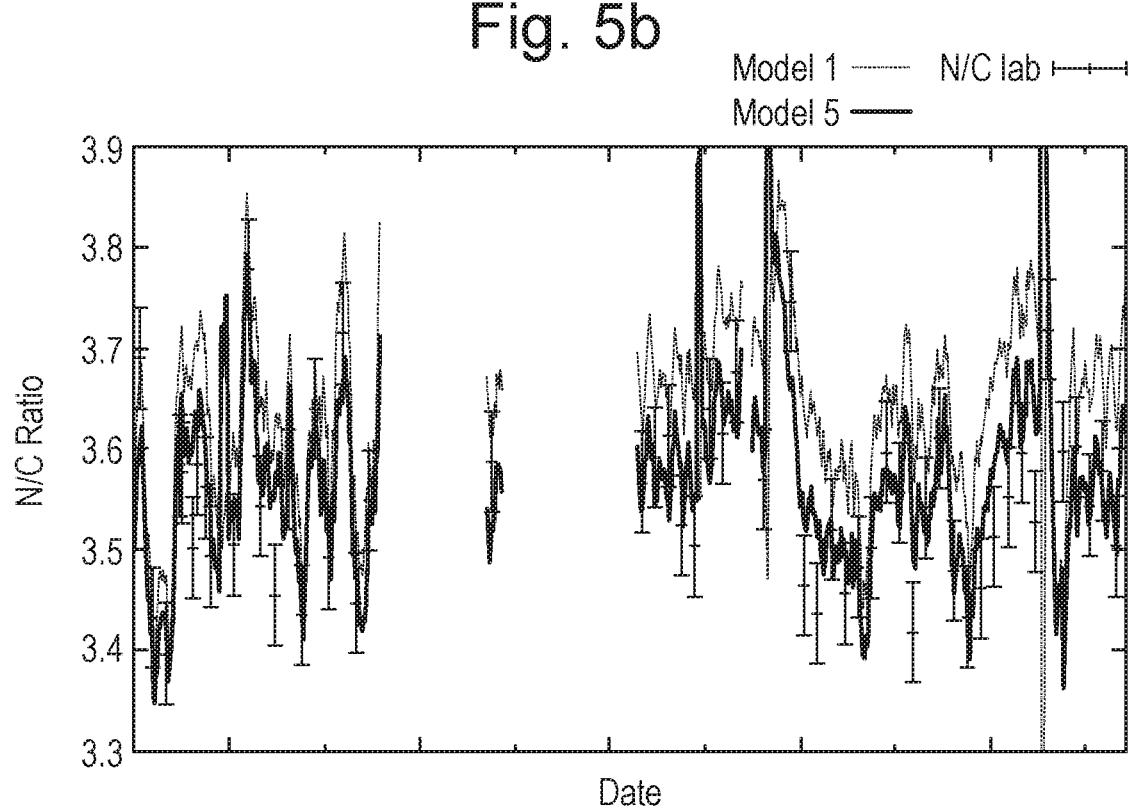

FIG. 5 shows a plot comparing model prediction data with offline measurement data. The plot is for the identified predictive model 5 for the first data set (FIG. 5(a)) and the second data set (FIG. 5(b)). As can be seen in FIG. 5(a), the identified model gives very similar predictions compared to the previously developed models for the first data set, of the first time period. FIG. 5(b) shows the same comparison for the second data set, this is the second time period. Here, the final model succeeds to eliminate the bias that has been observed using the initial models.

Figure 6:
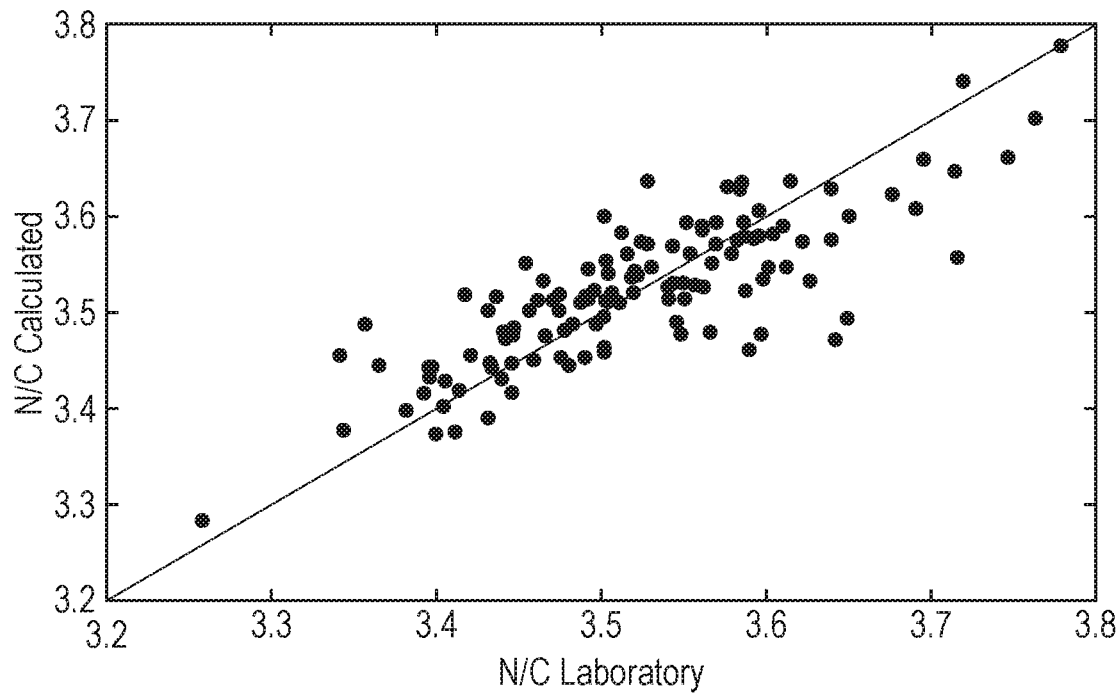
FIG. 6 shows a plot comparing model prediction data with offline measurement data.

FIG. 6 shows a plot comparing model prediction data with offline measurement data, more particularly N/C ratio values as the composition variable). In this figure, the model fit is visualized in a direct comparison plot, showing no significant indications of deviation from a linear relationship.

Optionally, the identified (empirical) models can be extended with an additional data set, for example from an original three months of data to six months of data. Further monitoring and validation against laboratory data is highly recommended. The determined model can be optimal with regard to predictive properties, given the set of available data. Model deterioration can still occur for instance with changing ambient conditions (towards summer) or operational changes. As a consequence of revamp activities, a recalibration of the model may be required.

Such a recalibration can be carried out manually or may be at least partially automatized. Such automation can be achieved by a computer program product configured to read in plant data (either directly from the plant or via data files), and perform the necessary steps for generating a new set of coefficients for the model. The computer program product may be configured to maintain a (file-based) database of historical data that can be reused in the calibration and validation process.

Furthermore, the concept of model-based N/C predicting can be extended to model-based predicting other composition variables, such as for instance a H/C ratio and/or an extent of reaction. An advantage of the N/C ratio as the selected composition variable is that it may be rather easy to predict from online measured process variable data.

The method and system, with or without physical modelling, greatly helps optimizing urea production in urea production plants.

Figure 7:
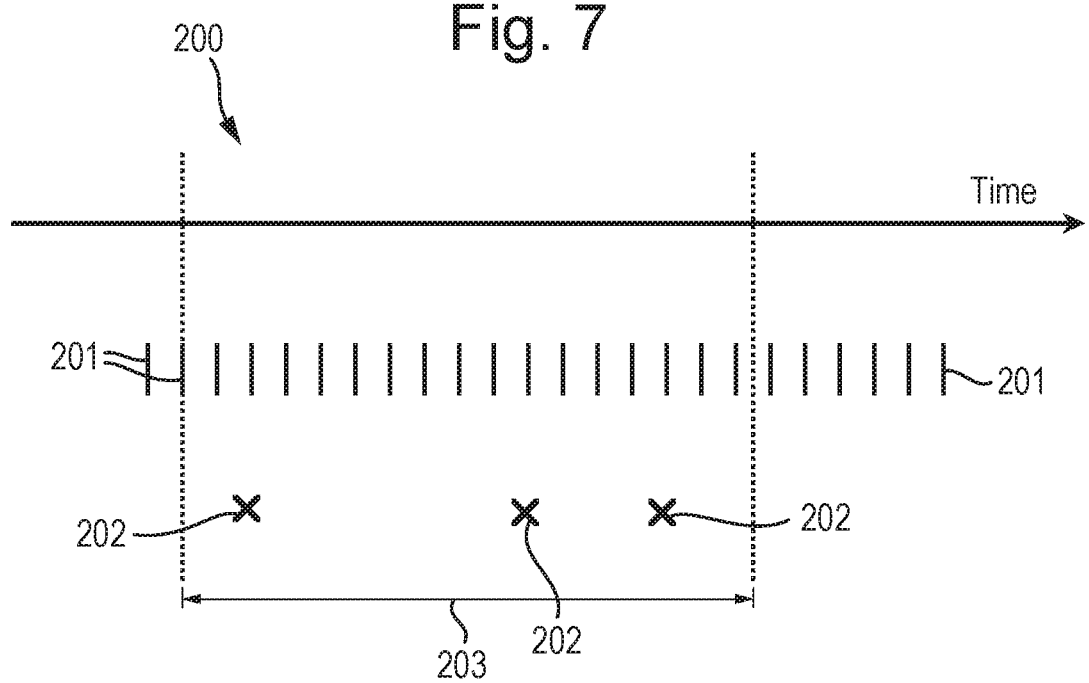
FIG. 7 shows a time plot with online and offline measurements.

FIG. 7 shows a time plot 200 with online measurements 201 and offline measurements 202. In this example, a plurality of online measurements 201 are carried out at subsequent time steps or time points. Furthermore, a plurality of offline measurements 202 are carried out at subsequent time steps. The model can be constructed on the basis of measurement data obtained in a first time period 203. It is appreciated that a different time period can also be used, for instance including a different time frame and/or other data. It is also envisaged that within a time period 203 particular online and/or offline measurement data is not taken into account for identifying the model. For instance, measurement data at certain time steps can be omitted (e.g. outliers).

The online measured process variables may be sampled at regular intervals. The time interval between subsequent offline measurements is typically larger compared to the time interval between online measured process variables. This can for instance be due to the fact that measurements of online process variables are rather easy to obtain compared to the offline measurements of the at least one composition variable (involving lab test).

The plurality of offline measurement data 202 can be obtained by sampling the at least one composition variable at different time points. The results of the offline measurements can be obtained for the time step at which an offline sample was taken for determining the at least one composition variable. However, the results of the offline measurement, for instance obtained by means of a lab test, can be obtained at a later time. The lab tests may take for example several hours, while the online measurements can be carried out frequently, or in real-time (or quasi real-time).

Figure 8:
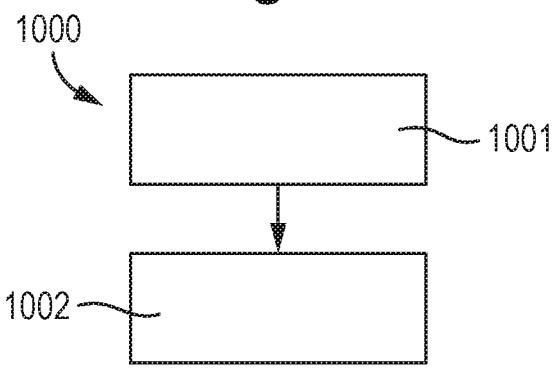
FIG. 8 shows a schematic diagram of a method.

FIG. 8 shows a schematic diagram of a method 1000 for controlling a urea production process based on a plurality of online measured process variables and a model. In a first step 1001, the model is used to estimate, during the urea production process, at least one composition variable indicative of a urea content on the basis of the plurality of online measured process variables. In a second step 1002, at least one of the plurality of online measured process variables is modified for ensuring that a value of the at least one composition variable is within a predetermined range. The model is obtainable by retrieving, over a first period of time during the urea production process, a plurality of online measurement data relating to a plurality of predetermined process variables by means of a plurality of sensors arranged in the urea synthesis plant, the plurality of predetermined process variables comprising at least one of the group comprising a flow rate, a liquid level, a temperature, and a pressure; retrieving, at different time steps within the first period of time, a plurality of offline measurement data of at least one composition variable; and processing the plurality of online and offline measurement data and performing a statistical analysis for identifying the model for predicting the at least one composition variable on the basis of the plurality of predetermined process variables.

Figure 9:
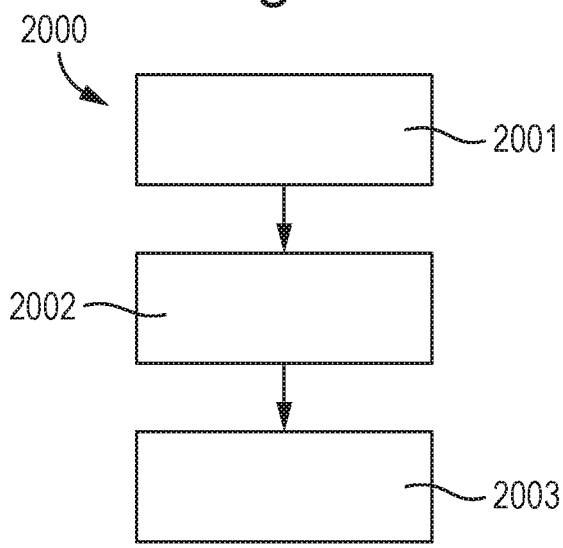
FIG. 9 shows a schematic diagram of a method.

FIG. 9 shows a schematic diagram of a method 2000 for obtaining a model for a urea production process. In a first step 2001, over a first period of time during the urea production process, a plurality of online measurement data relating to a plurality of predetermined process variables are retrieved by means of a plurality of sensors arranged in the urea synthesis plant, the plurality of predetermined process variables comprising at least one of the group comprising a flow rate, a liquid level, a temperature, and a pressure. In a second step 2002, at different time steps within the first period of time, a plurality of offline measurement data of at least one composition variable are retrieved. In a third step 2003, the plurality of online and offline measurement data are processed and a statistical analysis is performed for identifying the model for predicting the at least one composition variable on the basis of the plurality of predetermined process variables.

The orthogonal partial least squares algorithm can be implemented in different ways. As already indicated above, the data from measurements can be collection, (re-)arranged and/or down-sampled in various ways, if necessary.

It will be appreciated that the method may include computer implemented steps. All above mentioned steps can be computer implemented steps. Embodiments may comprise computer apparatus, wherein processes performed in computer apparatus. The invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program. For example, the carrier may comprise a storage medium, such as a ROM, for example a semiconductor ROM or hard disk. Further, the carrier may be a transmissible carrier such as an electrical or optical signal which may be conveyed via electrical or optical cable or by radio or other means, e.g. via the internet or cloud.

Some embodiments may be implemented, for example, using a machine or tangible computer-readable medium or article which may store an instruction or a set of instructions that, if executed by a machine, may cause the machine to perform a method and/or operations in accordance with the embodiments.

Various embodiments may be implemented using hardware elements, software elements, or a combination of both. Examples of hardware elements may include processors, microprocessors, circuits, application specific integrated circuits (ASIC), programmable logic devices (PLD), digital signal processors (DSP), field programmable gate array (FPGA), logic gates, registers, semiconductor device, microchips, chip sets, et cetera. Examples of software may include software components, programs, applications, computer programs, application programs, system programs, machine programs, operating system software, mobile apps, middleware, firmware, software modules, routines, subroutines, functions, computer implemented methods, procedures, software interfaces, application program interfaces (API), methods, instruction sets, computing code, computer code, et cetera.

Herein, the invention is described with reference to specific examples of embodiments of the invention. It will, however, be evident that various modifications, variations, alternatives and changes may be made therein, without departing from the essence of the invention. For the purpose of clarity and a concise description features are described herein as part of the same or separate embodiments, however, alternative embodiments having combinations of all or some of the features described in these separate embodiments are also envisaged and understood to fall within the framework of the invention as outlined by the claims. The specifications, figures and examples are, accordingly, to be regarded in an illustrative sense rather than in a restrictive sense. The invention is intended to embrace all alternatives, modifications and variations which fall within the spirit and scope of the appended claims. Further, many of the elements that are described are functional entities that may be implemented as discrete or distributed components or in conjunction with other components, in any suitable combination and location.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A virtual sensing method for controlling at least one composition variable in a urea production process, exclusively based on a plurality of online measured process variables and a model, wherein the model is used to estimate, during the urea production process, the at least one composition variable, on a basis of the plurality of online measured process variables, wherein the composition variable is selected from a group of a N/C ratio defined as a ratio between a total equivalent $NH_3$ and a total equivalent $CO_2$, a H/C ratio defined as a ratio between a total equivalent $H_2O$ and a total equivalent $CO_2$, and/or an extent of reaction defined as a ratio between urea and total equivalent $CO_2$, wherein the method includes modifying at least one of the plurality of online measured process variables for ensuring that a value of the at least one composition variable is within a predetermined range, wherein the model is obtainable by:

retrieving, over a first period of time during the urea production process, a plurality of online measurement data relating to a plurality of predetermined process variables by means of a plurality of sensors arranged in a urea synthesis plant, the plurality of predetermined process variables comprising at least one of a group consisting of a flow rate, a liquid level, a temperature, and a pressure;

retrieving, at time points within the first period of time, a plurality of offline measurement data of the at least one composition variable; and processing the plurality of online and offline measurement data and performing a statistical analysis for identifying the model, wherein the statistical analysis comprises an algorithm for performing a principal component analysis or a partial least squares analysis, wherein the process variables are selected from a group comprising a $CO_2$ feed flow, $CO_2$ flow to $CO_2$ stripper, a passivation air flow to reactor, a passivation air flow to any stripper, a carbamate recycle flow to carbamate condenser, a carbamate recycle flow to HP scrubber, a steam flow from carbamate condenser, a total flow of $NH_3$, a flow of $NH_3$ to carbamate condenser, a flow of $NH_3$ to carbamate ejector, a flow of $NH_3$ to reactor, a steam consumption of thermal stripper, a steam consumption to $CO_2$ stripper, steam to (any) strippers pressure, synthesis pressure at reactor top, carbamate condenser steam pressure, pressure of $NH_3$ feed, $CO_2$ stripper vapor exit temperature, $CO_2$ stripper liquid exit temperature, temperature of $NH_3$ feed, temperature carbamate, temperature at reactor top, temperature of middle of reactor, temperature of urea solution from reactor, temperature of bottom of reactor, thermal stripper vapor exit temperature, thermal stripper liquid exit temperature, pressure difference in urea reactor outlet valve, liquid level in reactor, liquid level in HP Scrubber, liquid level in HP Separator, wherein the plurality of online measured process variables obtained by means of online measurements over a second period of time different from the first period of time are provided as inputs to the identified model, wherein the model provides as an output at least one predicted composition variable, which is being controlled.

2. The method according to claim 1, wherein gathered sensor data from online measurements are stored in a data store, wherein a reduced data set is obtained from the data store, wherein the model is identified based on the reduced data set, the model providing a correlation between the reduced data set and the at least one composition variable.

3. The method according to claim 1, wherein a set of 2 to 6 process variables is used.

4. The method according to claim 1, wherein a set of process variables is used including at least one or more reactor temperatures and a steam flow to a thermal stripper.

5. The method according to claim 1, wherein a set of process variables is used including at least three of a group consisting of a steam consumption of a first $NH_3$ stripper, a temperature of the urea solution from a reactor, a temperature of a gas outlet of a second $NH_3$ stripper, a temperature of a $NH_3$ feed, a temperature in the middle of the reactor, and a temperature at the reactor top.

6. The method according to claim 1, wherein the urea production process is a $CO_2$ stripping process and/or thermal stripping process.

7. The method according to claim 1, wherein the urea production process is an isobaric double recycle process.

* * * * *